(12) United States Patent
Roos et al.

(10) Patent No.: US 7,994,300 B2
(45) Date of Patent: Aug. 9, 2011

(54) DIAGNOSTIC METHODS INVOLVING DETERMINING GENE COPY NUMBERS AND SNPS IN THE FCYRII/FCYRIII GENE CLUSTER, AND PROBES FOR USE IN SUCH METHODS TO DETECT SUSCEPTIBILITY TO AND TREATMENT EFFICACY IN AUTOIMMUNE DISEASES

(75) Inventors: Dirk Roos, Amsterdam (NL); Taco Willem Kuijpers, Amsterdam (NL)

(73) Assignee: Stichting Sanquin Bloedvoorziening, Amsterdam (NL)

( * ) Notice: Subject to any disclaimer, the term of this patent is extended or adjusted under 35 U.S.C. 154(b) by 49 days.

(21) Appl. No.: 12/158,623

(22) PCT Filed: Dec. 22, 2006

(86) PCT No.: PCT/NL2006/000662
§ 371 (c)(1),
(2), (4) Date: Oct. 14, 2008

(87) PCT Pub. No.: WO2007/073179
PCT Pub. Date: Jun. 28, 2007

(65) Prior Publication Data
US 2009/0263795 A1 Oct. 22, 2009

(30) Foreign Application Priority Data
Dec. 22, 2005 (EP) .................................. 05077984

(51) Int. Cl.
*C07H 21/02* (2006.01)
*C07H 21/04* (2006.01)
*C12Q 1/68* (2006.01)
*C12P 19/34* (2006.01)

(52) U.S. Cl. .......... 536/23.1; 536/24.3; 435/6; 435/91.2
(58) Field of Classification Search .................. None
See application file for complete search history.

(56) References Cited

U.S. PATENT DOCUMENTS
5,830,652 A 11/1998 Kimberly et al.
2004/0185045 A1 9/2004 Koenig et al.

FOREIGN PATENT DOCUMENTS
WO WO2005113815 12/2005

OTHER PUBLICATIONS

Boehringer Mannheim Biochemicals Catalog (1997) 'Hexanucleotide Mix', p. 95.*
Kyogoku, Chieko et al., "Fcgamma Receptor Gene Polymorphisms in Japanese Patients With Systemic Lupus Erythematosus: Contribution of FCBR2B to Genetic Susceptibility", Arthritis and Rheumatism May 2002, vol. 46, No. 5, May 2002, pp. 1242-1254, XP002430247, ISSN: 0004-3591, p. 1243, pp. 1245-125, col. 2 abstract.
Gittinger F. S. et al., "Quantitative determination of Fcgamma receptor genes by means of fluorescence-based real-time polymerase chain reaction", Tissue Antigens, Munksgaard, Copenhagen, DK, vol. 60, No. 1, Jul. 2002, pp. 64-70, XP002371642, ISSN: 0001-2815 abstract p. 66.
Jazwinska, E.C. et al., "Fcgamma RII Restriction fragment length polymorphism (RFLP): analysis in systemic lupus erythematosus and scleroderma and evidence of an alpha gene duplication", Clinical and Experimental Immunology, Oxford, GB, vol. 83, No. 1, Jan. 1991, pp. 47-51, XP001010748, ISSN: 0009-9104 abstract.
Reilly A. F. et al., "Variation in human FCGR2C gene copy number", Immunogenetics 1994, p. 456, XP008077969 whole document.
Su, Kaihong et al., "A Promoter Haplotype of the Immunoreceptor Tyrosine-Based Inhibitory Motif-Bearing FcgammaRIIB Alters Receptor Expression and Associates with Autoimmunity. II. Differential Binding of GATA4 and Yin-Yang1 Transcription Factors and Correlated Receptor Expression and Function.", Journal of Immunology (Baltimore, MD. 1950) Jun. 1, 2004, vol. 172, No. 11, pp. 7192-7199, XP002430249, issn. 0022-1767, abstract p. 7194.
Morgan, Ann W. et al., "Fcgamma receptor type IIIA is associated with rheumatoid arthritis in two distinct ethnic groups", Arthritis and Rheumatism, Lippincott, Philadelphia, US, vol. 43, No. 10, Oct. 2000, pp. 2328-2334, XP002288078, ISSN: 0004-3591 abstract.
Karassa, F.B. et al., "The role of FcgammaRIIA and IIIA polymorphism in autoimmune diseases", Biomedicine and Pharmacotherapy, Elsevier, Paris, FR., vol. 58, No. 5, Jun. 2004, pp. 286-291, XP002371643, ISSN: 0753-3322 abstract.
Morgan et al., "Analysis of Fcgamma receptor haplotypes in rheumatoid arthritis: FCGR3A remains a major susceptibility gene at this locus, with an additional contribution from FCGR3B", Arthritis Research & Therapy 2006, vol. 8, No. 1, Nov. 10, 2005, p. R5, XP002430250, ISSN: 1478-6362 abstract.
Dijstelbloem et al., "Inflammation in autoimmunity: receptors for IgG revisted", Trends in Immunology, Sep. 2001, vol. 22, No. 9 Sep. 2001 pp. 510-516, XP002430251, ISSN: 1471-4906 pp. 514-515.
Su, K. et al., "Genomic organization of classical human low-affinity Fcgamma receptor genes", Genes and Immunity, Oct. 2002, vol. 3, Suppl. 1, Oct. 2002, pp. S51-S56, XP002430252, ISSN: 1466-4879, abstract, pp. 53-54, table 2.

(Continued)

*Primary Examiner* — Stephen Kapushoc
(74) *Attorney, Agent, or Firm* — Hoffmann & Baron, LLP

(57) ABSTRACT

The invention relates to diagnostic methods to predict whether a subject is predisposed for acquiring a disease or to predict the therapy responsiveness of an individual patient. Provided is a method for determining whether a subject is predisposed for developing an autoimmune disease, comprising determining in a sample isolated from said subject the amount of intact genes, or gene products thereof, of the FcγRII/FcγRIII gene cluster, said gene cluster comprising the FCGR2C, FCGR3A, FCGR2A and FCGR3B genes encoding an activating FcγR, and FCGR2B encoding an inhibitory Fcγ R; and correlating said amount to the amount observed in a healthy population. Also provided is a method to predict the responsiveness of a subject to therapy with intravenous immunoglobulin (IVIg) therapy or a monospecific biological, such as a humanized or human monoclonal antibody or a chimeric molecule, comprising the C-terminal Fc-tail of IgG.

4 Claims, 9 Drawing Sheets

OTHER PUBLICATIONS

De Haas, et al., "Neutrophil Fcgamma RIIIb deficiency, nature, and clinical consequences: A study of 21 Individuals from 14 families.", Blood Sep. 15, 1995, vol. 86 No. 6, pp. 2403-2413, XP002430253, ISSN: 0006-4971, pp. 2409-241, col. 1.

Abe Jun et al., "Gene expression profiling of the effect of high-dose intravenous lg in patients with Kawasaki Disease.", Journal of Immunology, Williams & Wilkins Co., US, vol. 174, No. 9, May 1, 2005, pp. 5837-5845, XP002371640, issn: 0022-1767, the whole document.

Samuelsson et al., "Anti-inflammatory activity of IVIG mediated through the inhibitory Fc receptor", Science (New York, NY), Jan. 19, 2001, vol. 291, No. 5503, pp. 484-486, XP002430254, ISSN: 0036-8075, the whole document.

Ravetch J V et al., "Immune Inhibitory Receptors", Science (New York, NY), Oct. 6, 2000, vol. 290, No. 5489, pp. 84-89, XP002430255, ISSN: 0036-8075, the whole document.

* cited by examiner

```
                              SEQUENCE LISTING

<160> NUMBER OF SEQ ID NOS: 52

<210> SEQ ID NO 1
<211> LENGTH: 25
<212> TYPE: DNA
<213> ORGANISM: Artificial
<220> FEATURE:
<223> OTHER INFORMATION: Synthetic sequence: primer

<400> SEQUENCE: 1
tgaaacatac gttcccaaag agttt                                              25

<210> SEQ ID NO 2
<211> LENGTH: 26
<212> TYPE: DNA
<213> ORGANISM: Artificial
<220> FEATURE:
<223> OTHER INFORMATION: Synthetic sequence: primer

<400> SEQUENCE: 2
ctctccttct cagaaagtgt gcatat                                             26

<210> SEQ ID NO 3
<211> LENGTH: 28
<212> TYPE: DNA
<213> ORGANISM: Artificial
<220> FEATURE:
<223> OTHER INFORMATION: Synthetic sequence: primer

<400> SEQUENCE: 3
ctctcaagct ccttgggctt cctcttct                                           28

<210> SEQ ID NO 4
<211> LENGTH: 25
<212> TYPE: DNA
<213> ORGANISM: Artificial
<220> FEATURE:
<223> OTHER INFORMATION: Synthetic sequence: primer

<400> SEQUENCE: 4
accccccttt cctgcaaacc tctgc                                              25

<210> SEQ ID NO 5
<211> LENGTH: 21
<212> TYPE: DNA
<213> ORGANISM: Artificial
<220> FEATURE:
<223> OTHER INFORMATION: Synthetic sequence: primer

<400> SEQUENCE: 5
tggcgattaa gtcaaattcg c                                                  21
```

```
<210> SEQ ID NO 6
<211> LENGTH: 25
<212> TYPE: DNA
<213> ORGANISM: Artificial
<220> FEATURE:
<223> OTHER INFORMATION: Synthetic sequence: primer

<400> SEQUENCE: 6 cccctagta ccctgacaat gtatt                                          25

<210> SEQ ID NO 7
<211> LENGTH: 37
<212> TYPE: DNA
<213> ORGANISM: Artificial
<220> FEATURE:
<223> OTHER INFORMATION: Synthetic sequence: primer

<400> SEQUENCE: 7
gagatcaagc ttatgtcaaa tatttaagca agcctac                            37

<210> SEQ ID NO 8
<211> LENGTH: 37
<212> TYPE: DNA
<213> ORGANISM: Artificial
<220> FEATURE:
<223> OTHER INFORMATION: Synthetic sequence: primer

<400> SEQUENCE: 8
gagatcctcg agacttgtcc atgatatagt tagacac                            37

<210> SEQ ID NO 9
<211> LENGTH: 26
<212> TYPE: DNA
<213> ORGANISM: Artificial
<220> FEATURE:
<223> OTHER INFORMATION: Synthetic sequence: primer

<400> SEQUENCE: 9
gaaaatatgt ggttggagag ctcatt                                        26

<210> SEQ ID NO 10
<211> LENGTH: 22
<212> TYPE: DNA
<213> ORGANISM: Artificial
<220> FEATURE:
<223> OTHER INFORMATION: Synthetic sequence: primer

<400> SEQUENCE: 10
ccgagtgaag atcccctttt ta                                            22

<210> SEQ ID NO 11
<211> LENGTH: 23
<212> TYPE: DNA
<213> ORGANISM: Artificial
<220> FEATURE:
<223> OTHER INFORMATION: Synthetic sequence: primer

<400> SEQUENCE: 11
atcattgtgg ctgtggtcat tgc                                           23

<210> SEQ ID NO 12
<211> LENGTH: 23
<212> TYPE: DNA
<213> ORGANISM: Artificial
<220> FEATURE:
<223> OTHER INFORMATION: Synthetic sequence: primer

<400> SEQUENCE: 12
```
tcaggtagat gtttttatca tcg 23

<210> SEQ ID NO 13
<211> LENGTH: 24
<212> TYPE: DNA
<213> ORGANISM: Artificial
<220> FEATURE:
<223> OTHER INFORMATION: Synthetic sequence: primer

<400> SEQUENCE: 13
ggaaaaagcg catttgagcc aatc 24

<210> SEQ ID NO 14
<211> LENGTH: 25
<212> TYPE: DNA
<213> ORGANISM: Artificial
<220> FEATURE:
<223> OTHER INFORMATION: Synthetic sequence: primer

<400> SEQUENCE: 14
ggaaatacga gatcttccct ctctg 25

<210> SEQ ID NO 15
<211> LENGTH: 40
<212> TYPE: DNA
<213> ORGANISM: Artificial
<220> FEATURE:
<223> OTHER INFORMATION: Synthetic sequence: probe

<400> SEQUENCE: 15
gtctcagaat gtatgtccca gaaacctgtg gctgcttcaa 40

<210> SEQ ID NO 16
<211> LENGTH: 40
<212> TYPE: DNA
<213> ORGANISM: Artificial
<220> FEATURE:
<223> OTHER INFORMATION: Synthetic sequence: probe

<400> SEQUENCE: 16
atagtcatcc cagcactgtg ccaacgtcca gtgggtttta 40

<210> SEQ ID NO 17
<211> LENGTH: 40
<212> TYPE: DNA
<213> ORGANISM: Artificial
<220> FEATURE:
<223> OTHER INFORMATION: Synthetic sequence: probe

<400> SEQUENCE: 17
tctgtgactc tgacatgcca gggggctcgc agccctgaga 40

<210> SEQ ID NO 18
<211> LENGTH: 41
<212> TYPE: DNA
<213> ORGANISM: Artificial
<220> FEATURE:
<223> OTHER INFORMATION: Synthetic sequence: probe

<400> SEQUENCE: 18
aaatcccaga aattctccca tttggatccc accttctcca t 41

<210> SEQ ID NO 19
<211> LENGTH: 40
<212> TYPE: DNA
<213> ORGANISM: Artificial

```
<220> FEATURE:
<223> OTHER INFORMATION: Synthetic sequence: probe

<400> SEQUENCE: 19
ggagaaggtg ggatccaaac gggagaattt ctgggatttt                          40

<210> SEQ ID NO 20
<211> LENGTH: 40
<212> TYPE: DNA
<213> ORGANISM: Artificial
<220> FEATURE:
<223> OTHER INFORMATION: Synthetic sequence: probe

<400> SEQUENCE: 20
tcattgcgac tgctgtagca gccattgttg ctgctgtagt                          40

<210> SEQ ID NO 21
<211> LENGTH: 40
<212> TYPE: DNA
<213> ORGANISM: Artificial
<220> FEATURE:
<223> OTHER INFORMATION: Synthetic sequence: probe

<400> SEQUENCE: 21
agatggctgg gattactcac ctcaaattgg gcagccttca                          40

<210> SEQ ID NO 22
<211> LENGTH: 40
<212> TYPE: DNA
<213> ORGANISM: Artificial
<220> FEATURE:
<223> OTHER INFORMATION: Synthetic sequence: probe

<400> SEQUENCE: 22
atagcacagc tgtccacaga agcatatgac cccaaggctg                          40

<210> SEQ ID NO 23
<211> LENGTH: 40
<212> TYPE: DNA
<213> ORGANISM: Artificial
<220> FEATURE:
<223> OTHER INFORMATION: Synthetic sequence: probe

<400> SEQUENCE: 23
ctgaaagaca caaaaaaccg cagaggaccc gggaggtctt                          40

<210> SEQ ID NO 24
<211> LENGTH: 40
<212> TYPE: DNA
<213> ORGANISM: Artificial
<220> FEATURE:
<223> OTHER INFORMATION: Synthetic sequence: probe

<400> SEQUENCE: 24
ctgaaagaca cagaaaaccc cagaggaccc gggaggtctt                          40

<210> SEQ ID NO 25
<211> LENGTH: 40
<212> TYPE: DNA
<213> ORGANISM: Artificial
<220> FEATURE:
<223> OTHER INFORMATION: Synthetic sequence: probe

<400> SEQUENCE: 25
ggcagagaga ggaggtagca tgaagaagag gaagcccagg                          40
```

<210> SEQ ID NO 26
<211> LENGTH: 40
<212> TYPE: DNA
<213> ORGANISM: Artificial
<220> FEATURE:
<223> OTHER INFORMATION: Synthetic sequence: probe

<400> SEQUENCE: 26
gtggctgtgg tcactgggac tgctgtagcg gccattgttg                40

<210> SEQ ID NO 27
<211> LENGTH: 40
<212> TYPE: DNA
<213> ORGANISM: Artificial
<220> FEATURE:
<223> OTHER INFORMATION: Synthetic sequence: probe

<400> SEQUENCE: 27
gtggctgtgg tcactgggat tgctgtagcg gccattgttg                40

<210> SEQ ID NO 28
<211> LENGTH: 40
<212> TYPE: DNA
<213> ORGANISM: Artificial
<220> FEATURE:
<223> OTHER INFORMATION: Synthetic sequence: probe

<400> SEQUENCE: 28
caatcccact aatcctgatg aggctgacaa agttggggtg                40

<210> SEQ ID NO 29
<211> LENGTH: 40
<212> TYPE: DNA
<213> ORGANISM: Artificial
<220> FEATURE:
<223> OTHER INFORMATION: Synthetic sequence: probe

<400> SEQUENCE: 29
caatcaccta ttcacttctc atgcacccgg atgctctgga                40

<210> SEQ ID NO 30
<211> LENGTH: 40
<212> TYPE: DNA
<213> ORGANISM: Artificial
<220> FEATURE:
<223> OTHER INFORMATION: Synthetic sequence: probe

<400> SEQUENCE: 30
gaaggctgcc caatttgaga tgagtaatcc cagccatctc                40

<210> SEQ ID NO 31
<211> LENGTH: 40
<212> TYPE: DNA
<213> ORGANISM: Artificial
<220> FEATURE:
<223> OTHER INFORMATION: Synthetic sequence: probe

<400> SEQUENCE: 31
gccatcagaa agagacaact tgaagaaacc aacaatgact                40

<210> SEQ ID NO 32
<211> LENGTH: 40
<212> TYPE: DNA
<213> ORGANISM: Artificial
<220> FEATURE:
<223> OTHER INFORMATION: Synthetic sequence: probe

<400> SEQUENCE: 32

```
gccatcagaa agagacaacc tgaagaaacc aacaatgact                               40

<210> SEQ ID NO 33
<211> LENGTH: 40
<212> TYPE: DNA
<213> ORGANISM: Artificial
<220> FEATURE:
<223> OTHER INFORMATION: Synthetic sequence: probe

<400> SEQUENCE: 33
ttgggcttcc tcttcctcac gctacctcct ctctctgccc                               40

<210> SEQ ID NO 34
<211> LENGTH: 40
<212> TYPE: DNA
<213> ORGANISM: Artificial
<220> FEATURE:
<223> OTHER INFORMATION: Synthetic sequence: probe

<400> SEQUENCE: 34
tccaggctct ttccttcctg gtcctgttct atggtggggc                               40

<210> SEQ ID NO 35
<211> LENGTH: 40
<212> TYPE: DNA
<213> ORGANISM: Artificial
<220> FEATURE:
<223> OTHER INFORMATION: Synthetic sequence: probe

<400> SEQUENCE: 35
ctcaatggta cagggtgctc gagaaggaca gtgtgactct                               40

<210> SEQ ID NO 36
<211> LENGTH: 40
<212> TYPE: DNA
<213> ORGANISM: Artificial
<220> FEATURE:
<223> OTHER INFORMATION: Synthetic sequence: probe

<400> SEQUENCE: 36
ctacttctgc aggggggcttt ttgggagtaa aaatgtgtct                              40

<210> SEQ ID NO 37
<211> LENGTH: 40
<212> TYPE: DNA
<213> ORGANISM: Artificial
<220> FEATURE:
<223> OTHER INFORMATION: Synthetic sequence: probe

<400> SEQUENCE: 37
ctacttctgc aggggggcttg ttgggagtaa aaatgtgtct                              40

<210> SEQ ID NO 38
<211> LENGTH: 40
<212> TYPE: DNA
<213> ORGANISM: Artificial
<220> FEATURE:
<223> OTHER INFORMATION: Synthetic sequence: probe

<400> SEQUENCE: 38
agactggaag gaccataaat ttaaatggag aaaggaccct                               40

<210> SEQ ID NO 39
<211> LENGTH: 40
<212> TYPE: DNA
<213> ORGANISM: Artificial
```

```
<220> FEATURE:
<223> OTHER INFORMATION: Synthetic sequence: probe

<400> SEQUENCE: 39
tccacccatc tctgtcacct gccagtttcc ttttcttgaa                              40

<210> SEQ ID NO 40
<211> LENGTH: 40
<212> TYPE: DNA
<213> ORGANISM: Artificial
<220> FEATURE:
<223> OTHER INFORMATION: Synthetic sequence: probe

<400> SEQUENCE: 40
ctcaatggta cagcgtgctt gagaaggaca gtgtgactct                              40

<210> SEQ ID NO 41
<211> LENGTH: 40
<212> TYPE: DNA
<213> ORGANISM: Artificial
<220> FEATURE:
<223> OTHER INFORMATION: Synthetic sequence: probe

<400> SEQUENCE: 41
agactggaag gaccataaac ttaaatggag aaaggaccct                              40

<210> SEQ ID NO 42
<211> LENGTH: 40
<212> TYPE: DNA
<213> ORGANISM: Artificial
<220> FEATURE:
<223> OTHER INFORMATION: Synthetic sequence: probe

<400> SEQUENCE: 42
cactgcaaat cgacacctat taatgggtct cacctcccaa                              40

<210> SEQ ID NO 43
<211> LENGTH: 40
<212> TYPE: DNA
<213> ORGANISM: Artificial
<220> FEATURE:
<223> OTHER INFORMATION: Synthetic sequence: probe

<400> SEQUENCE: 43
ccaccaggag gtcttcctag gcaaggacct gggtggcttt                              40

<210> SEQ ID NO 44
<211> LENGTH: 40
<212> TYPE: DNA
<213> ORGANISM: Artificial
<220> FEATURE:
<223> OTHER INFORMATION: Synthetic sequence: probe

<400> SEQUENCE: 44
gagggtgcat ctgcccggaa gactcagact cctgcagccc                              40

<210> SEQ ID NO 45
<211> LENGTH: 40
<212> TYPE: DNA
<213> ORGANISM: Artificial
<220> FEATURE:
<223> OTHER INFORMATION: Synthetic sequence: probe

<400> SEQUENCE: 45
aagaaggccc tggtcttcct gtttacgttc ttgtcagaac                              40
```

```
<210> SEQ ID NO 46
<211> LENGTH: 40
<212> TYPE: DNA
<213> ORGANISM: Artificial
<220> FEATURE:
<223> OTHER INFORMATION: Synthetic sequence: probe

<400> SEQUENCE: 46
gcggacgctg cgtggaacat tttccgcgag tactggagtt                              40

<210> SEQ ID NO 47
<211> LENGTH: 40
<212> TYPE: DNA
<213> ORGANISM: Artificial
<220> FEATURE:
<223> OTHER INFORMATION: Synthetic sequence: probe

<400> SEQUENCE: 47
gccattgagg tctataaaat tatagagaaa gttgattacc                              40

<210> SEQ ID NO 48
<211> LENGTH: 40
<212> TYPE: DNA
<213> ORGANISM: Artificial
<220> FEATURE:
<223> OTHER INFORMATION: Synthetic sequence: probe

<400> SEQUENCE: 48
cgcttccgca tgttcagcaa gcagggagtg ttgactctgg                              40

<210> SEQ ID NO 49
<211> LENGTH: 40
<212> TYPE: DNA
<213> ORGANISM: Artificial
<220> FEATURE:
<223> OTHER INFORMATION: Synthetic sequence: probe

<400> SEQUENCE: 49
agggtgacct gatagctgct caggctcggc tgaaggacct                              40

<210> SEQ ID NO 50
<211> LENGTH: 40
<212> TYPE: DNA
<213> ORGANISM: Artificial
<220> FEATURE:
<223> OTHER INFORMATION: Synthetic sequence: probe

<400> SEQUENCE: 50
agacccgact ggtggagatt gacaatggga agcagagtga                              40

<210> SEQ ID NO 51
<211> LENGTH: 40
<212> TYPE: DNA
<213> ORGANISM: Artificial
<220> FEATURE:
<223> OTHER INFORMATION: Synthetic sequence: probe

<400> SEQUENCE: 51
agacccatgt tcttgacatt gagcagcgac tacaaggtgt                              40

<210> SEQ ID NO 52
<211> LENGTH: 40
<212> TYPE: DNA
<213> ORGANISM: Artificial
```

-continued

```
<220> FEATURE:
<223> OTHER INFORMATION: Synthetic sequence: probe

<400> SEQUENCE: 52
gtaacaaccg ggattcttca gcactcaacc acagctccaa                    40
```

US 7,994,300 B2

DIAGNOSTIC METHODS INVOLVING DETERMINING GENE COPY NUMBERS AND SNPS IN THE FCYRII/FCYRIII GENE CLUSTER, AND PROBES FOR USE IN SUCH METHODS TO DETECT SUSCEPTIBILITY TO AND TREATMENT EFFICACY IN AUTOIMMUNE DISEASES

This application is the U.S. National Phase of, and Applicants claim priority from, International Application Number PCT/NL2006/000662 filed 22 Dec. 2006, and European Application bearing Serial No. 05077984.2 filed 22 Dec. 2005, which are incorporated herein by reference.

BACKGROUND OF THE INVENTION

The invention relates to the fields of immunology and molecular medicine. In particular, it relates to diagnostic methods involving the determination the amount of intact genes of the FcγRII/FcγRIII gene cluster and to uses thereof in disease management, for example to predict whether a subject is predisposed for acquiring a disease or to predict the therapy responsiveness of an individual patient. It also relates to probes and nucleic acid constructs for use in such methods.

Sequencing the human genome has prompted many technical advances and stimulated the discoveries of various genomic landmarks. One area is the development of a dense set of polymorphic markers for gene mapping. The most common form of DNA sequence variation is a single nucleotide polymorphism (SNP) but, in addition, there are microsatellite repeat polymorphisms and insertion/deletion polymorphisms. Whereas SNPs and microsatellites have been very well characterized in terms of their genomic locations and their frequencies in different populations, insertion/deletion polymorphisms are less well characterized. Recent papers (see for example Sebat J. et al. Large-scale copy number polymorphism (CNP) in the human genome. Science 2004; 305: 525-528) described the identification of large (several kilobases to megabases) deletions and duplications of DNA fragments when genomes of normal individuals were compared. The identification and characterization of CNPs show that in addition to single-nucleotide differences, genomes of unrelated individuals have large regions of thousands to millions of nucleotides that are different.

From a functional perspective, gene copy number differences can contribute to variation in gene expression. CNPs of coding and regulatory regions are likely to affect expression of genes at the transcript and/or protein levels. Gene expression studies have shown that subtle differences in expression levels of genes have significant consequences. For example, copy number polymorphism of the defensin gene cluster probably accounts for natural variation in the expression level of DEFB4 which, in turn, might account for individual differences in immune defence (Linzmeier et al., Genomics. 2005; 86:423-30). Furthermore, Gonzalez et al. (Science. 2005; 307:1434-40) reported that possession of a CCL3L1 copy number lower than the population average is associated with markedly enhanced HIV/acquired immunodeficiency syndrome (AIDS) susceptibility. Cappuzzo et al. (J. Natl Cancer Inst. 2005; 97:643-55) disclosed that patients with advanced non-small-cell lung cancer whose tumour cells contain extra copies of the epidermal growth factor receptor (EGFR) gene may be more likely to respond to the drug gefitinib (Iressa), and suggested that this high gene copy number may be an effective predictor of gefitinib efficacy.

Thus, evidence is accumulating that CNPs and their overall effect on gene expression contributes significantly to the variation that underlies individual differences in predisposition to complex diseases.

SUMMARY OF THE INVENTION

It is a goal of the present invention to provide new diagnostic markers for autoimmune diseases, in particular markers that can be used to predict whether a) a subject is predisposed for developing an autoimmune disease and, b) once a subject has been diagnosed with an autoimmune disease, whether the individual subject will follow a severe or a benign course of the disease or whether the disease will develop into a chronic form and, c) whether the individual subject diagnosed with an autoimmune disease will respond to certain types of therapy.

These goals are met by the finding that genes of the FcγRII/FcγRIII gene cluster are suitably used as prognostic markers for major autoimmune diseases, as well as for predicting disease development and/or therapy responsiveness to intravenous immunoglobulin (IVIg) therapy. As is described in detail below, the inventors set out to measure the copy number and SNPs of genes in the human FcγRII and FcγRIII gene cluster at chromosome 1q21-23. Using primers designed to hybridize in the regions of the FcγRII and RIII genes that are specific for the genes, the copy number of FcγRII and RIII genes in human subjects suffering from an auto-inflammatory disease was determined. More specifically, data obtained from patients suffering from an auto-inflammatory disease in childhood—the so-called Kawasaki Disease- and from patients having immune thrombocytopenic purpura (ITP) were compared with those of control subjects.

Kawasaki Disease is an acute febrile syndrome in infancy, which is characterized by a vasculitis of mainly the medium-sized arteries. Since there is no specific test to diagnose the disease, diagnosis is made on clinical criteria. In this form of pediatric vasculitis, high-doses of IVIg infusions are used as standard treatment to prevent coronary artery lesion. As is disclosed herein, Kawasaki patients were on average found to have an amount different from the usual number of two FCGR2B genes per genome, when normalized to several reference genes (CYBB as X-linked gene, SRY as Y-linked gene and ALB encoding the plasma protein human serum albumin, as an autosomal gene). Variations of the gene copy number in patients and control subjects are shown in the Examples below.

ITP is a disease characterised by thrombocytopenia with otherwise normal cell lineages and no other explanation for the isolated thrombocytopenia. Destruction of autoantibody-sensitised platelets by FcγR-bearing phagocytic cells in the reticuloendothelial system plays an important role, although the exact pathophysiology of this autoimmune disorder is not precisely known. The role of Fc receptors is underscored by the fact that intravenous immunoglobulin (IVIg) treatment, via blockade of the Fc receptors for IgG, and splenectomy (removal of the platelet-destructing organ) are effective treatment options.

Previous studies concerning polymorphisms in the FCGR gene cluster in ITP patients show conflicting results. In a study involving 116 ITP patients, the present inventors found an increased variation in the FCGR2 and FCGR3 gene cluster in Caucasian patients as compared to healthy Caucasian controls. For example, 82% of a healthy population is homozygous for a SNP that converts a glutamine in the FGCR2C open reading frame (ORF) into a stop codon, rendering FCGR2C a non-expressed pseudogene. The remainder (18%) of the healthy population contains FCGR2-ORF. In contrast, 35% of the ITP patients were found to carry at least one FCGR2C-ORF allele, which results in the expression of a functionally activating FcγRIIc. Furthermore, a significant difference in genotype and allele frequency for the promoter polymorphism −386G/C was observed. The genotype −386CC was rare, and only observed in an ITP patient. In the same series of DNA samples, we confirmed the previously observed over-representation of the SNP in FCGR3A encoding the FcγRIIIa-158V variant, being most prevalent in ITP of childhood-onset (p=0.0005) and not ITP of adult-onset (p=0.3).

These studies indicate that the relative amounts of activating versus inhibitory FcγRs are indicative for developing an autoimmune disease. It has been previously reported that antibodies against FcγRII used could make a distinction between health and disease in autoimmunity or otherwise, but this is incorrect. Although the relevance of such imbalance between activating and inhibitory FcγRII receptors has been repeatedly suggested, to date all these studies were based on the use of non-specific antibodies that, first of all, can not differentiate between the different FcγRII isoforms [Nakatani et al. Clin. Exp. Immunol. 1999; 117:418-22; Van Wijngaarden et al., Rheumatology 2003; 42:681-8]. Moreover, the authors often refer to staining patterns by monoclonal antibodies (MoAbs) on immune cells that are known to have highly variable expression levels of FcγRs because of in-vivo or in-vitro activation by growth factors, cytokines or inflammatory triggers. Furthermore, the present inventors show that the recently developed "FcγRIIb-specific MoAbs" that have always been assumed to bind exclusively to FcγRIIb, also bind to FcγRIIc-expressing cells. Because of the identical extracellular domains of FcγRIIb and FcγRIIc, these observations are to be expected in individuals carrying the uncommon FCGR2C-ORF allele and hence expressing FcγRIIc. In sum, a genetic approach to quantify the variability in CNPs and SNPs in the FCGR gene cluster, preferably in a single assay as proposed by the present inventors, is the most reliable way of testing disease susceptibility, disease severity and treatment efficacy in IgG-mediated processes from changes in this gene cluster.

DESCRIPTION OF THE INVENTION

Herewith, the invention provides a method for determining whether a subject is predisposed for developing an autoimmune disease, comprising determining in a sample isolated from said subject the amount of the genes, or of gene products thereof, in the FcγRII/FcγRIII gene cluster, said gene cluster comprising the FCGR2C, FCGR3A, FCGR2A and FCGR3B genes, encoding an activating FcγR, and FCGR2B encoding an inhibitory FcγR; and correlating said amount to the amount observed in a healthy population, wherein an increased amount of a gene encoding an activating FcγR (i.e. FCGR2C, FCGR3A, FCGR2A and FCGR3B) or gene product thereof, and/or a decreased amount of gene encoding an inhibitory FcγR (i.e. FCGR2B), or gene product thereof, is indicative of having an increased chance of developing an autoimmune disease.

The term "gene product" as used herein refers to products resulting from expression of said genes (RNA or protein) and thus comprises transcripts (mRNA) and translated proteinaceous substances encoded by one of the FCGR2A, FCGR2B, FCGR2C, FCGR3A and FCGR3B genes (also referred to as FcγRIIa, FcγRIIb, FcγRIIc, FcγRIIIa and FcγRIIIb, respectively). Preferably, it refers to mRNA, in view of lack of specific probes which can distinguish between the gene products at the protein level.

The expression "activating FcγR" refers to an FcγR which is functionally active and capable of providing stimulatory or positive signalling. It also comprises "hyperactive" variants or mutant receptors that display a higher activity as compared to their normal counterpart, for example resulting from a SNP. Likewise, an "inhibitory FcγR" refers to an FcγR which is functionally active and capable of providing inhibitory or negative signalling.

According to the invention, a gene can be a genomic sequence such as a cDNA sequence. A "sample isolated from said subject" can be any type of biological sample or biopsy comprising cellular material, plasma, serum, urine, sputum, liquor, etc. of the subject. Nucleic acids can be extracted by methods known in the art to yield a nucleic acid sample, for example using commercial DNA or RNA extraction kits.

As used herein, the term "autoimmune disease" refers to any disease or disorder in which the progression from benign autoimmunity to pathogenic autoimmunity occurs. An estimated 5-10% of all people suffer from inflammations or a reactivity that may in many instances be related to the formation of antibodies against an individual's own tissue components. Autoimmunity is caused by a complex interaction of multiple gene products, unlike immunodeficiency diseases, where a single dominant genetic trait is often the main disease determinant. In one embodiment, the autoimmune disease is an organ-specific autoimmune disease.

Examples of auto-immune diseases are organ-specific (i.e. type 1 diabetes mellitus (IDDM1), Addison's disease, Graves' disease, Hashimoto's thyroiditis, autoimmune hypoparathyroidism, autoimmune hypophysitis, autoimmune oophoritis, autoimmune orchitis, autoimmune polyendocrinopathy, autoimmune syndrome type 1 (PAS-1), type 2 (PAS-2) and type 3 (PAS 3), polymyositis/dermatomyositis, bullous pemphigoid, epidermolysis bullosa acquisita, pemphigus foliaceous, pemphigus vulgaris, alopecia greata, vitiligo, autoimmune hearing loss, Meniere's syndrome, Mooren's ulcer, multiple sclerosis (MS), myasthenia gravis, Vogt-Koyanagi-Harada disease, autoimmune myocarditis, pernicious anemia, autoimmune hepatitis, primary biliary cirrhosis, celiac disease, inflammatory bowel disease (IBD), Crohn's disease, Guillain-Barré syndrome, chronic inflammatory demyelinating polyneuropathy, IgA nephropathy, Goodpasture's syndrome,) In another embodiment, the autoimmune disease is of a systemic and/or hematological nature (i.e. idiopathic thrombocytopenic purpura, aplastic anemia, autoimmune hemolytic anemias, antiphospholipid syndrome, autoimmune lymphoproliferative syndrome, polyarteritis nodosa, polyglandular Bechet's disease, Takayasu's arteritis, Kawasaki's disease (KD), rheumatoid arthritis (RA), sarcoidosis, scleroderma, Sjögren's syndrome, systemic lupus erythematosus (SLE), Reiter's syndrome, ankylosing spondilitis, Wegener's granulomatosis, Churg-Strauss syndrome, giant cells arteritis). In addition to these more or less 'classical' examples of auto-immune disease, recent data indicate that some psychiatric or affective disorders also have an inflammatory component.

In a preferred aspect, the invention provides a method for predicting the predisposition to Kawasaki disease, Systemic Lupus Erythematosus (SLE), Idiopathic Thrombocytopenic Purpura (ITP) and/or rheumatoid arthritis (RA).

It is known that the intact FCGR2A, FCGR2C (e.g. FCGR2C-ORF), FCGR3A and FCGR3B genes encode activating FcγRII and FcγRIII receptors, while FCGR2B encodes an inhibitory FcγRIIb. Without wishing to be bound by theory, the inventors propose that a change in the balance between the amount or activity of activating FcγRII and FcγRIII receptors on the one hand and the inhibitory FcγRIIb receptor on the other hand is associated with autoimmune disease. This is in line with the identification of patients with auto-inflammatory Kawasaki disease (KD) or ITP having three instead of the usual two alleles of the FCGR3A gene for the activating FcγRIIIa receptor, and the increase in FCGR2C-ORF observed in both KD and ITP.

In a preferred embodiment, a method of the invention therefore comprises determining the relative amount of activating versus inhibitory Fcγ receptors, and comparing the relative amount found in a matching healthy control population. An increase in the ratio of activating over inhibitory receptors is an indicator of having or developing an autoimmune disease.

It will be understood by the skilled person that a method of the invention can involve the detection of different activating and/or inhibitory. genes or products thereof. In one embodiment, a method of the invention comprises determining the amount of intact FCGR2C gene or gene product, preferably FCGR2C-ORF. Since the FCGR2C is not expressed as a functional activating receptor in the majority of a healthy population being homozygous for the pseudogene of FCGR2C due to the FCGR2C$^{stop}$ allele, the presence of an intact FCGR2C-ORF allele will shift the balance to a relative excess of stimulatory signals.

As indicated above, in a method according to the invention the amount of an activating and/or inhibitory FcγRII or FcγRIII gene (product) can be determined at the genomic, transcriptional and/or the translational level (i.e. protein expression). Detection at the genomic level is preferred since genomic analyses are typically fast, reliable and do not require highly specialized personnel. For example, it may entail the determination of the FcγR gene copy number polymorphisms (CNPs) and/or the analysis of genomic alterations, for example SNPs, which directly or indirectly affect gene transcription or function of the gene product.

Methods for detecting CNPs are known in the art. The majority of the known methods are based on quantitative polymerase chain reaction (Q-PCR) methods. The Q-PCR reaction is characterised by an exponential increase in the amount of PCR product in the early cycles, which reaches a plateau phase as the reaction products become inhibitory. The higher the starting copy number of the target gene, the sooner the increase in fluorescence is detected and a lower threshold cycle number (Ct) value is reached. The possibility of direct measurement of the PCR product accumulated after each amplification cycle, without any intermediate steps, ensures the high specificity of Q-PCR assays. Currently four different types of probes, TaqMan® (Applied Biosystems, Foster City, Calif., USA), Molecular Beacons, Scorpions®, FRET probes and the DNA-binding dye SYBR® Green (Molecular Probes), are generally used for Q-PCR. SYBR Green is a fluorogenic dye that exhibits little fluorescence when in solution, but emits a strong fluorescent signal upon binding to double-stranded DNA.

Studies using Q-PCR for detecting gene copy number involve relative quantitative methods that rely on detection of a reference gene to calculate the gene copy number, i.e. the gene of interest is normalized to an appropriate endogenous (housekeeping) gene. To date, the ALB gene encoding albumin is generally being used for direct comparison and quantification as a golden standard reference. For example, Thiel et al. (2002) used ALB as an internal reference gene to detect the number of genes encoding peripheral myelin protein 22 (PMP22) on chromosome 17p11.2-12, which gene is responsible for the hereditary neuropathy Charcot-Marie-Tooth (CMT1A). The same approach with albumin as internal standard was applied by Schaeffeler et al. (2003) to determine the CYP2D6 gene dosage per genome to study drug metabolism phenotypes. Both Thiel and Schaeffeler used Taqman technology with Taqman probes. A similar approach with ALB as a reference gene was undertaken by Layfield et al. (2003) using LightCycler technology with SYBR Green to quantitate the copy number of EGF receptor genes in colorectal adenocarcinoma.

In all these studies, the number of genes for albumin was assumed to be 2 in total—i.e. one located on the maternal chromosome number 4 and one on the paternal chromosome number 4 in any individual. This assumption has been accepted as a "fact" without proper verification or unequivocal proof. However, the present inventors observed that the gene copy number of ALB varies considerably (2 or more) among human individuals and is thus not as stable as expected. It appeared that the ALB gene could not be used as reliable reference gene in gene dosage studies. Therefore, they set out to identify a reference gene that has a lower variance in copy number as compared to the "golden standard ALB gene" encoding human serum albumin, which can serve as a more reliable reference gene in gene dosage studies. This goal was met by the observation that the CYBB gene, localized in humans on the X chromosome, has a remarkable low variance in copy number. Using CYBB-specific primers that anneal in or around exon 8 of the CYBB gene, the inventors screened more than 100 controls (males and females), more than 200 obligate carriers (females), more than 300 male patients, and about 30 foetuses as a routine prenatal diagnostic effort. This screening revealed no variance in CYBB copy number at all.

Accordingly, the invention provides a method for determining the copy number of the FCGR2A, FCGR2B, FCGR2C, FCGR3A and FCGR3B target genes, or orthologues thereof, in the genome of a subject, comprising detecting the amount of said target genes relative to the amount of a reference gene in a nucleic acid sample of said subject, wherein the reference gene is the CYBB gene or an orthologue thereof. Preferably, the subject is a mammalian subject, more preferably a human subject.

The CYBB gene (gene aliases are CGD; NOX2; GP91-1; GP91PHOX was identified at Xp21. It encodes the CYBB protein, also known as glycoprotein-91 (gp91)-phox, cytochrome $b_{558}$, beta polypeptide, cytochrome $b_{-245}$, beta polypeptide. Cytochrome $b_{558}$ is composed of cytochrome $b_{558}$ alpha (CYBA) and beta (CYBB) chain. It has been proposed as a primary component of the microbicidal oxidase system of phagocytes. CYBB deficiency is one of six described biochemical defects associated with chronic granulomatous disease (CGD).

The method of the invention preferably involves the detection of one or more target genes and said CYBB gene using Q-PCR technology.

Other methods for quantitative nucleic acid analysis can also be used, such as Southern blotting or multiplex ligation-dependent probe amplification (MLPA). The skilled person will be able to design suitable sets of PCR primers for the detection of the target gene(s) and the CYBB gene. In one embodiment, CYBB is detected using CYBB-specific primers in or around exon 8, as this was found to give a high PCR efficiency. Suitable probes for detecting amplified PCR products include SYBR Green I Dye, hydrolysis probes or hybridisation probes. The two most used quantitative PCR technologies are the Taqman™ technology of Applied Biosystems and the LightCycler® technology of Roche. In one aspect, LightCycler®™ technology is employed. The system works with glass capillaries. Hot and cold air allowing rapid ramping—30 cycles can be performed within 20 minutes.

The PCR process is monitored by fluorescence quantification of DNA-binding dyes for general detection of double-stranded DNA, or, with hybridization probes, to monitor the amount of a specific target sequence. The probes are irradiated with a blue-light-emitting diode (470 nm), which excites yellow dyes including fluorescein (FAM, FITC) and SybrGreen. The emitted fluorescent light is detected in three channels for green light (530 nm, fluorescein), red light (640 nm, LightCycler® Red 640) and near infrared (710 nm, LC Red 705).

In a preferred embodiment, a method of the invention comprises determining the copy number of one or more intact target genes of the FcRII/FcγRIII gene cluster by PCR, using a recombinant nucleic acid construct ("reference construct") comprising a known number of copies of genes selected from the group consisting of FCGR2A, FCGR2B, FCGR2C, FCGR3A and FCGR3B, or orthologues thereof, fragment(s) thereof as well as a known number of copies of the reference gene, or fragment thereof. Therefore, the invention provides a recombinant nucleic acid "reference construct" comprising two segments, a first segment comprising the gene of interest selected from the group consisting of FCGR2A, FCGR2B, FCGR2C, FCGR3A and FCGR3B, or orthologues thereof, or a fragment thereof, and a second segment comprising a reference gene, or a fragment thereof, preferably wherein the ratio of said first to said second fragment is 1:1.

The reference construct is for example a plasmid or vector comprising said at least said first and second segment. The first segment with the target gene sequence(s) and the second segment with the reference gene sequence can be ligated substantially directly to each other or they can be spaced by a stretch of amino acids. The spacing between the two segments is not of particular relevance as long as both segments are present on the same construct. The order of the first and second segment within the construct is irrelevant. For reasons given above, a nucleic acid construct of the invention preferably comprises as a reference gene the human CYBB, or a relevant orthologue thereof in case the copy number of a non-human subject is to be determined. Orthologues of human CYBB are known in the art. In a specific aspect, the reference construct comprises at least 50 base pairs of human CYBB. It was found that ligation of 198 bp of exon 8 of the CYBB gene to a fragment of a target gene (e.g. FCGR gene, see further below) gave very good results.

From the comparison of the reference gene (segment) and the target gene (segment) in a known ratio (e.g. 1:1) on the one hand with the target DNA containing an unknown gene copy number for these genes, the exact differences in PCR amplification efficiency and therefore the exact gene ratio's can be calculated from the LightCycler or Taqman technique. A major advantage of using a reference construct of the invention when determining the copy number of a target gene resides in the fact that the external construct containing both target and reference gene in every run corrects for differences in PCR amplification efficiency and gene quantity caused by variations in the initial sample amount. This application makes the gene dosage analysis robust and trustworthy.

Therefore, in one embodiment the invention provides a method for determining whether a person is predisposed for developing an autoimmune disease as described herein above, said method comprising determining, preferably by Q-PCR, the amount of FCGR2C, FCGR2B, FCGR2A, FCGR3A and FCGR3B target genes (or orthologues thereof in case the method is applied to non-human subjects), and the presence of a reference gene in a nucleic acid sample of said subject, using as external control a recombinant nucleic acid construct comprising at least a fragment of the target gene and a fragment of the reference gene.

The skilled person will understand that a detection method of the invention using CYBB as reference gene and/or the recombinant control DNA is not limited with respect to a particular target gene or group of target genes of which the copy number is to be determined.

In one embodiment, a method of the invention involves SNP analysis of one or more regions, e.g. the promoter region, controlling the rate and extent of FcγR gene transcription. Polymorphisms in the promoter region at nucleotide−386 and −120 are linked to transcriptional activity of the FCGR2B gene (Su et al., J Immunol. 2004; 172:7186-91). Four different haplotypes have been identified, i.e. 2B.1 or "wild type" (−386G/−120T); 2B.2 (−386C/−120T), which may be a more frequent polymorphism in the promoter for the FCGR2C (pseudo)gene; 2B.3 (−386G/−120A); and 2B.4 (−386C/−120A). The 2B.4 haplotype was reported to have enhanced transcriptional activity compared to the 2B.1 haplotype. The differences in the ratios of FcγRIIa/FcγRIIb2 mRNA in neutrophils (see further below) were found to be related to these polymorphisms. A strong association with the 2B.4 haplotype and the 1:1 FcγRIIa/FcγRIIb2 mRNA ratio was found, whereas the 2:1 ratio was highly associated and the 3:1 and 4:1 FcγRIIa/FcγRIIb2 mRNA ratios even strictly associated with the 2B.1 haplotype with low transcriptional activity. These findings indicate that the increased transcription of FCGR2B in neutrophils is dependent to the 2B.4 haplotype, resulting in lower FcγRIIa/FcγRIIb2 mRNA ratios. The fact that mononuclear cells of the same donors show widely variable and non-fixed FcγRIIa/FcγRIIb2 ratios, demonstrates additional genetic factors to be identified.

A PCR method of particular interest for the present invention involves multiplex ligation-dependent probe amplification (MLPA) technology, originally described by Schouten et al. (Nucleic Acids Res 2002; 30:e57). MPLA is highly specific and requires a minimum of 20 ng of genomic DNA to be analysed. For instance, it can be used for the relative quantification of 40 different DNA sequences in an easy to perform reaction and uses more than one reference gene. Known applications of MLPA technique include the detection of exon deletions and duplications in the human oncogenes, detection of trisomies such as Down's syndrome, characterisation of chromosomal aberrations in cell lines and tumour samples as well as SNP or mutation detection. Relative quantification of mRNAs by MLPA is another application described elsewhere (Eldering et al., Nucleic Acids Res 2003; 31:e153).

In MLPA, not the sample nucleic acids but the probes that are added to the samples are amplified by PCR and quantified. Amplification of the probes depends on the presence of probe target sequences in the sample. Each probe set consists of two oligonucleotides, two synthetic probes or one synthetic probe and one M13-derived probe that hybridize to adjacent sites of the target sequence. These hybridized probes are ligated, permitting subsequent amplification. All ligated probes have identical end sequences that allow simultaneous PCR amplification by the use of one universal primer pair. By varying the probe length for each probe, this will give rise to an amplification product of unique size between 130 and 480 bp. Probe target sequences are typically small (50-100 nucleotides). The prerequisite of a ligation reaction provides the opportunity to discriminate between single nucleotide differences. SNP analysis is conveniently done by MLPA technology using target-specific MLPA probes. The inventors designed two novel mixes of MLPA probes to detect FCGR-specific sequences within exons, introns and promoter regions, as well as to detect FCGR2B-, FCGR2C-, FCGR3A-, and FCGR3B-specific SNPs (see FIG. 1 and Table 2). This is a major achievement, since the FCGR2A, FCGR2B and FCGR2C genes show an extremely high degree of homology, as do the FCGR3A and FCGR3B genes. In one embodiment, the invention provides a method for the CNP and/or SNP detection at the genomic level by MLPA analysis, wherein at least one of the probes as indicated in bold in Table 2A or 2B is used. Preferably, it comprises the use of all probes indicated in bold in Table 2A and/or 2B. More preferably, it comprises, in one reaction tube, the use of all probes of Table 2A (Probe Mix 1) and in a separate reaction tube the probes of Table 2B (Probe Mix 2). Tables 2C, 2D and 2E show the target sequences that are detected by the probes of Tables 2A and 2B, i.e. the probe sequence is complementary to the target sequence. Also provided herein is an MLPA probe that is suitably used in a method of the invention, said probe being selected from Tables 2C, 2D or 2E. In a specific aspect, the invention provides an FCGR2 probe capable of detecting a target sequence as set out in Table 2C. In another embodiment, the invention provides an FCGR3 probe capable of detecting a target sequence as shown Table 2D. Also provided is a control probe which detects a target sequence of those of Table 2E. Furthermore, there is provided the use of at least one of the target sequences depicted in Tables 2C, 2D and 2E in a method for determining a CNP or a SNP in the FcγRII/FcγRIII gene cluster.

It is also possible to detect aberrant amounts of either activating and/or inhibitory receptors at the transcriptional, i.e. mRNA level. Still further, gene product analysis can be performed at the protein level using specific probes for the individual FcγR gene products, such as MoAbs or (affinity-purified) polyclonal antibodies. However, as indicated above, antibodies described thus far cannot discriminate between the extracellular domains of the different members of the gene cluster. Therefore, in the absence of specific reagents that can discriminate between the different gene products at the protein level, analysis at the protein level is preferably accompanied by analysis at the genetic (DNA and/or mRNA) level.

Conventional nucleic acid (DNA, RNA) and protein analytical methods can be used to detect the amount of an FcγRII or RIII gene product according to the invention. For a review on quantitative analysis of nucleic acids, see Ding and Cantor (2004), J. Biochem. Mol.Biol. Vol 37, No. 1, pp. 1-10. (Q-)PCR analysis is particularly convenient for the purpose of the present invention. Preferred PCR techniques include Light-Cycler and MPLA technology.

Only for the purpose of illustration, the method of the invention is exemplified by the analysis of material obtained from two types of patients, each suffering from a distinct autoimmune disease. However, it will be clear for the skilled person that the underlying concept of the present invention is applicable to any type of autoimmune disease.

A specific aspect relates to a method for determining whether a subject is predisposed for developing ITP, comprising determining in a sample isolated from said subject the amount of genes, or gene products thereof, of the FcγRII/FcγRIII gene cluster, said FcγRII/FcγRIII gene cluster comprising the FCGR2C, FCGR3A, FCGR2A and FCGR3B genes encoding an activating FcγR, and FCGR2B encoding an inhibitory FcγR; and correlating said amount to the amount observed in a healthy population; wherein an increased amount of genes encoding an activating FcγR, or gene products thereof, and/or a decreased amount of gene encoding an inhibitory FcγR, or gene product thereof, is indicative of having an increased chance of developing ITP. Preferably, the method comprises detecting the amount of the FCGR2C-ORF gene (product), determining the allele frequencies of the FCGR3A SNP for the FcγRIIIa-158F and/or FcγRIIIa-158V variant(s), and/or determining the allele frequency for the promoter polymorphism −386G/C. More preferably, it comprises at least determining the presence of the FCGR2C-ORF gene or gene product, e.g. messenger RNA or the FcγRII protein.

Another specific aspect relates to a method for determining whether a subject is predisposed for developing Kawasaki Disease (KD), comprising determining in a sample isolated from said subject the amount of genes, or gene products thereof, of the FcγRII/FcγRIII gene cluster, said FcγRII/FcγRIII gene cluster comprising the FCGR2C, FCGR3A, FCGR2A and FCGR3B genes encoding an activating FcγR, and FCGR2B encoding an inhibitory FcγR; and correlating said amount to the amount observed in a healthy population; wherein an increased amount of genes encoding an activating FcγR, or gene products thereof, and/or a decreased amount of gene encoding an inhibitory FcγR, or gene product thereof, is indicative of having an increased chance of developing KD.

Variation in FCGR2B exon-3 probe binding has never been observed in any healthy control or members of several multigeneration families tested for inheritance patterns within the FCGR gene cluster. Preferably, the method comprises detecting the amount of FCGR2B, for example by detection of gain or loss of FCGR2B exon-3 amplification product, the FCGR2C-ORF gene (product), and/or the amount of FCGR3A (e.g. by CNP analysis) More preferably, a method for determining the predisposition for KD comprises at least determining the presence of FCGR2B exon-3 probe binding and the FCGR2C-ORF gene or gene product, e.g. messenger RNA or the FcγRIIb and/or FcγRIIc protein.

In a still further aspect, the invention relates to the management of autoimmune diseases. Most autoimmune diseases have a high morbidity, with crippling results for the patients, and cause a high incidence of mortality. The quality of life of these patients is seriously diminished, resulting in high socio-economical and health costs. Treatment may consist of symptomatic treatment such as hormone substitution in case of endocrinological gland disease or immunosuppressive therapy in case of more wide-spread disease to suppress progression of disease and (multi)organ dysfunction. The major drawback of general immunosuppression consists of a reduction of the host's defence mechanisms against various infectious agents (even resulting in opportunistic infections) and an increased risk of malignancies.

For some autoimmune diseases, treatment with intravenous immunoglobulin (IVIg) preparations or so-called IgG-based treatment consisting of murine MoAbs, humanized MoAbs, or (recombinant) human MoAbs or chimeric molecules with an Fc region to interact with any of the FcγRs (collectively referred to as 'biologicals') is the standard treatment of choice.

These preparations have been found to modulate the autoimmune phenomena without these afore-mentioned disadvantages. The use of high-dose IVIg for the treatment of immune thrombocytopenic purpura (ITP) was first reported more than two decades ago. After the therapeutic benefit of IVIg was established in ITP, it was then successfully used to treat many other autoimmune diseases. Although a complete definition of the mechanism of IVIg action is still lacking, extensive research suggests that IVIg may achieve its therapeutic effects through multiple mechanisms. IVIg exerts immunomodulatory effects that may include antiidiotypic neutralization of antiplatelet antibodies, stimulation of FcγRIIb expression, and inhibition of FcγR-mediated platelet destruction (Jin and Balthasar, Hum Immunol. 2005; 66:403-10).

As with the other treatment modalities, IVIg works for many, but not for all patients. The increasing number of reports of IVIg for the treatment of various autoimmune diseases and the general good clinical outcome of this therapeutic modality strongly indicate that IVIg has a role in these conditions. Hence, it is important to identify those patients that would benefit most from this treatment.

The present inventors observed a correlation between the amount of certain FcγRII/FcγRIII gene cluster products and the responsiveness to IVIg therapy or treatment with biologicals. For example, an increased amount of activating FcγR gene product, such as the presence of FCGR2C-ORF, and/or a decreased amount of inhibitory FcγRIIb gene product was found to be indicative of a poor response to IVIg therapy. Accordingly, the invention also provides a method to predict the responsiveness of a patient suffering from an autoimmune disease to therapy with intravenous immunoglobulin (IVIg) or a monospecific biological, such as a humanized monoclonal antibody or a chimeric molecule, comprising the C-terminal Fc-tail of IgG, comprising determining in a sample isolated from said subject the amount of intact genes, or gene products thereof, of the FcγRII/FcγRIII gene cluster, said FcγRII/FcγRIII gene cluster comprising the FCGR2C, FCGR3A, FCGR2A and FCGR3B genes encoding an activating FcγR, and FCGR2B encoding an inhibitory FcγR; and correlating said amount to the amount observed in a healthy population; wherein an increased amount of genes encoding an activating FcγR, or gene products thereof, and/or a decreased amount of gene encoding an inhibitory FcγR, or gene product thereof, is indicative of having a reduced chance of being responsive to said therapy.

Thus, provided is a method to predict the responsiveness of a patient to IVIg therapy, comprising the determination of the amount of genes, or gene products thereof, of the FcγRII/FcγRIII gene cluster, said FcγRII/FcγRIII gene cluster comprising the FCGR2C, FCGR3A, FCGR2A and FCGR3B genes encoding an activating FcγR, and FCGR2B encoding an inhibitory FcγR; and correlating said amount to the amount observed in a healthy population; wherein an increased amount of genes encoding an activating FcγR, or gene products thereof, and/or a decreased amount of gene encoding an inhibitory FcγR, or gene product thereof, is indicative of having a reduced chance of being responsive to said therapy.

Similar to what is described above, the analysis of the gene can be done at the genomic, or at the corresponding transcriptional and/or the translational level. Also, the various abovementioned combinations of genes and/or gene products can be detected. In one embodiment, the responsiveness to IVIg therapy or to monospecific biologicals is predicted by determining the amount of intact FCGR2C gene or gene product, preferably FCGR2C-ORF. Since the FcγRIIc is not expressed as a functional activating receptor in the majority of a healthy population due to the homozygosity for the pseudogene of FCGR2C (containing the FCGR2C$^{stop/stop}$ SNP), the presence of an intact FCGR2C-ORF gene will shift the balance to a relative excess of stimulatory signals. Because of the very high degree of homology between the extracellular domains of all receptors within the FcγRII/FcγRIII gene cluster, these receptors can at present not all be distinguished from each other by means of detection with MoAbs or polyclonal antibodies. As a consequence, an antibody that is used e.g. therapeutically to provide inhibitory signals via the inhibitory FcγRIIb receptor will also bind to the extracellular domain of the activating FCGR2C-ORF gene product, FcγRIIc. Binding to and activation of the FcγRIIc receptor by the therapeutic compound will not only counteract the effect mediated by FcγRIIb but it may even cause a net increase in activating signals, thereby worsening the disease condition. Thus, in one embodiment the invention provides a method to identify a subject that is likely to react negatively to therapy with IVIg therapy or biologicals, comprising detecting the presence or absence of the FCGR2C-ORF gene or gene product. Preferably, it is detected at the genetic level, optionally in combination with detection at the protein level, for example using an antibody capable of recognizing FcγRIIc protein. Example 4 herein below exemplifies how the FCGR2C-ORF gene may be detected.

In a particular aspect, predicting IVIg/biologicals therapy responsiveness comprises determining the copy number of said gene, for example using MPLA technology. MPLA probes provided herein are suitably used.

The patient to be considered for IVIg therapy is for example a subject, preferably a human child, diagnosed with Kawasaki Disease. Other patients that would benefit from the predictive method include patients with Idiopathic Thrombocytopenic Purpura, Systemic Lupus Erythematosus or Rheumatoid Arthritis.

Experimental Section

Fc receptors are proteins on the surface of all leukocytes and platelets that are able to bind immunoglobulins, especially when these are complexed with antigens in an immune complex. Fc-gamma receptors (FcγR) specifically bind immunoglobulin G (IgG). FcγR exist in a number of isoforms, namely FcγR type I, type II and type III. FcγRI is a receptor with a high affinity for IgG, whereas FcγRII and FcγRIII have a lower affinity. The distribution of these receptors over the various types of leukocytes is shown in Table 1.

TABLE 1

FcγR diversity and cell distribution

| Subclass | genes | cellular distribution | motif |
|---|---|---|---|
| FcγRI | FCGR1 | monocytes, macrophages, IFNγ- or G(M)-CSF-treated neutrophils | ITAM in γ-chains |
| FcγRIIa | FCGE2A | monocytes, macrophages, neutrophils, B lymphocytes and platelets | ITAM in FcγR |
| FcγRIIb | FCGR2B | B lymphocytes (macrophages, neutrophils) | ITIM in FcγR |
| FcγRIIc | FCGE2C | ??? | ITAM in FcγR |
| FcγRIIIa | FCGR3A | NK cells, macrophages | ITAM in γ chains |
| FcγRIIIb | FCGR3B | neutrophils, IFNγ-treated eosinophils | ITAM in γ chains |

Binding of IgG (in a complex) to the FcγRs in general induces cell activation, as, for instance, uptake of the immune complex, release of cytotoxic proteins and generation of reactive oxygen species by phagocytic leukocytes (neutrophils, eosinophils and monocytes/macrophages). Also the immunoglobulin production, the cytokine production and the cytotoxic reactions of specific subpopulation of lymphocytes are induced by Fcγ receptors. This cell activation is mediated by a so-called immunoreceptor tyrosine-based activation motif (ITAM) located in the cytoplasmic tail of the FcγR itself or in cytoplasmic regions of associated proteins, which becomes phosphorylated after crosslinking of FcγR's on the cell surface by the immune complex. However, there is also an FcγR that dampens the immune response. This FcγRIIb contains an inhibitory ITIM motif in its cytoplasmic tail, which associates with tyrosine phosphatases that counteract the phosphorylation of the ITAM motif. Thus, a balanced immune response is mediated by an equilibrium between signals from the activating FcγRs and the inhibiting FcγRIIb.

Recently, the importance of the inhibitory FcγRIIb has become clear from studies with knock-out mice. These mice, which lack the FcγRIIb, were subjected to treatment that induces inflammatory reactions in the skin, the lung, the joints or the kidney. It turned out that the knock-out mice developed excessive auto-immune and chronic inflammatory reactions, which clearly proves that dampening of the immune response by signals from FcγRIIb is indispensable for a normal physiologic reaction to an antigenic challenge (Clynes et al., J. Exp. Med. 1999; 189: 179; Yuasa et al., J. Exp. Med. 1999; 189: 187; Bolland & Ravetch, Immunity 2000; 13: 277). For that reason, patients with the auto-immune disease SLE have been investigated for the presence of SNPs in their FcγRIIb gene FCGR2B. However, until now, no clear correlation was found between the occurrence of certain polymorphisms and the susceptibility to this disease.

Cytoband 1q21-23 is one of the regions implicated in susceptibility to multiple autoimmune diseases. The FcγRII/III genes are located at 1q23, and a new family of genes, Fc receptor-like genes (FCRLs, also known as FcRHs), clusters nearby at 1q21 (Davis et al., 2001, 2002). FCRLs have high structural homology with the classical genes encoding the FcγRs, although the ligands and function of the FcR-like proteins are not yet known. Region 1q23 is a candidate locus for susceptibility to SLE, and variants in the classical FcγR II/III genes partially account for disease susceptibility (Tsao, 2003; Ravetch and Bolland., 2001; Kyogoku et al., 2002). Although 1q21-23 is a good candidate region for containing rheumatoid arthritis-susceptibility genes, the association of classical FcγRs with disease susceptibility remains controversial (Nieto et al., 2001; Radstake et al., 2003).

We studied genes in the FcγR cluster and changes therein in detail in Kawasaki disease, a major autoinflammatory disease, and ITP, an autoimmune hematological disease.

Kawasaki disease is an acute febrile syndrome in infancy, which is characterized by a vasculitis of mainly the medium-sized arteries. Since there is no specific test to diagnose the disease, diagnosis is made on clinical criteria. First, fever must be present for more than five days, not responding to antibiotics or antipyretics. Furthermore, at least four of the five following symptoms must be present: lymphadenopathy, edema and erythema of hand and feet, a polymorphous rash, bilateral conjunctivitis, enanthema and inflammation of the mucous membranes (Kawasaki, 1979, Burns & Glode, 2004). The incidence of Kawasaki disease is 5-17 per 100 000 in Europe and the United States, mostly in children under the age of five years. For unknown reasons the incidence in Japan is 135 per 100 000. In approximately 25% of the children the vasculitis will lead to coronary aneurysmatic lesions (CAL) as detected by echocardiography, which may develop during the acute stage of the disease when untreated. This makes it the leading cause of acquired heart disease in children. The coronary vasculitis may cause death by sudden rupture when becoming giant in diameter, or cause flow disturbance and thrombosis within the aneurysmatic lesions, resulting in acute myocardial infarction. Following recovery, Kawasaki disease may eventually lead to heart disease in adolescence or young adulthood due to progressive stenosis and calcification of affected coronary arteries.

Therapy consists of a single high-dose of IVIg (2 g/kg) infused in 8-12 hours and aspirin, resulting in a decrease of complications to 5-16% (Newburger et al., 1991, Tse et al., 2002). To date little is known about the working mechanisms of IVIg and why this therapy is successful in many and fails in other patients with Kawasaki disease, especially in the very young. Inadequate handling or insufficient clearance of microbial antigens by IgG-dependent mechanisms might, in certain individuals, be responsible for this difference.

ITP patients suffer from a bleeding tendency. The low number of platelets in the circulation of these patients is caused by the presence of auto-antibodies against platelets. Standard therapy is again IVIg or corticosteroids.

Systemic lupus erythematosus (SLE) is the archetypal autoimmune disease given its complex clinical and molecular manifestations. Like the other rheumatic diseases, appropriate management is critically dependent upon the proper assessment of disease activity, organ damage, and quality of life. SLE patients suffer from an auto-immune disease characterized by the production of antinuclear auto-antibodies caused by a failure of B cell tolerance and tissue deposition of immune complexes. Thus, the B lymphocyte plays a key role in SLE pathogenesis by both autoantibody-dependent and autoantibody-independent mechanisms. Additionally, aberrant interactions between B and T cells are critical to disease emergence and progression. New agents that directly target immune cells abnormal in SLE include the B-cell depleting or modulating antibodies, rituximab (anti-CD20) and epratuzumab (anti-CD22) and the anti-dsDNA tolerogen LJP394. Immune cells can also be manipulated indirectly through cytokine effects. For B cells, anti-BAFF (B-cell activation factor of the tumor necrosis family) provides an example of this approach. Other, more pleiotropic cytokines can likewise be blocked in SLE. In addition to the blockade of interleukin-10 (IL-10), the first anti-cytokine approach examined, it is mainly anti-TNF therapy that has come into focus, holding promise for some patients with lupus nephritis. Many additional cytokines, such as IL-6, IL-18, and the type I interferons, represent interesting future targets in which antagonism depend on neutralizing properties as well as FcγR-mediated effects.

Rheumatoid arthritis, juvenile idiopathic arthritis, the seronegative spondyloarthropathies including psoriatic arthritis, and SLE are all examples of rheumatic diseases in which inflammation is associated with skeletal pathology. Although some of the mechanisms of skeletal remodeling are shared among these diseases, each disease has a unique impact on articular bone or on the axial or appendicular skeleton. The blockade of TNF by so-called biologicals (anti-TNF humanized murine monoclonal antibodies or chimeric molecules engineered as N-terminal binding domains derived from authentic receptors and C-terminal FcγR-binding Fc-tail) with strong TNF-binding properties have significant impact on the therapy of a number of chronic autoimmune diseases, such as the aforementioned rheumatic diseases as well as inflammatory bowel disease. The experience with this therapy in rheumatoid arthritis (RA) and Crohn's disease (CD) have spread its application into other autoimmune diseases, and has led to augmented therapeutic benefit. Other promising approach has been to block co-stimulatory interactions between T and B cells in rheumatic diseases, for example by inhibiting the CD40-CD40 ligand pathway with anti-CD40 ligand monoclonal antibody or the B7 pathway with the chimera CTLA4-Ig. There are still many limitations, but the prospects for the future of such biologicals is intriguing. The Fcγ-binding properties of these biologicals make the therapeutic efficacy subject to the same influence of FcγRs as demonstrated in case of IVIg via FcγR-mediated activities.

Several probes within each separate gene can be used to determine the CNPs and the SNPs. Note that the probe that recognizes FCGR3B-NA1 is the same that recognizes FCGR3A.

Figure 2:
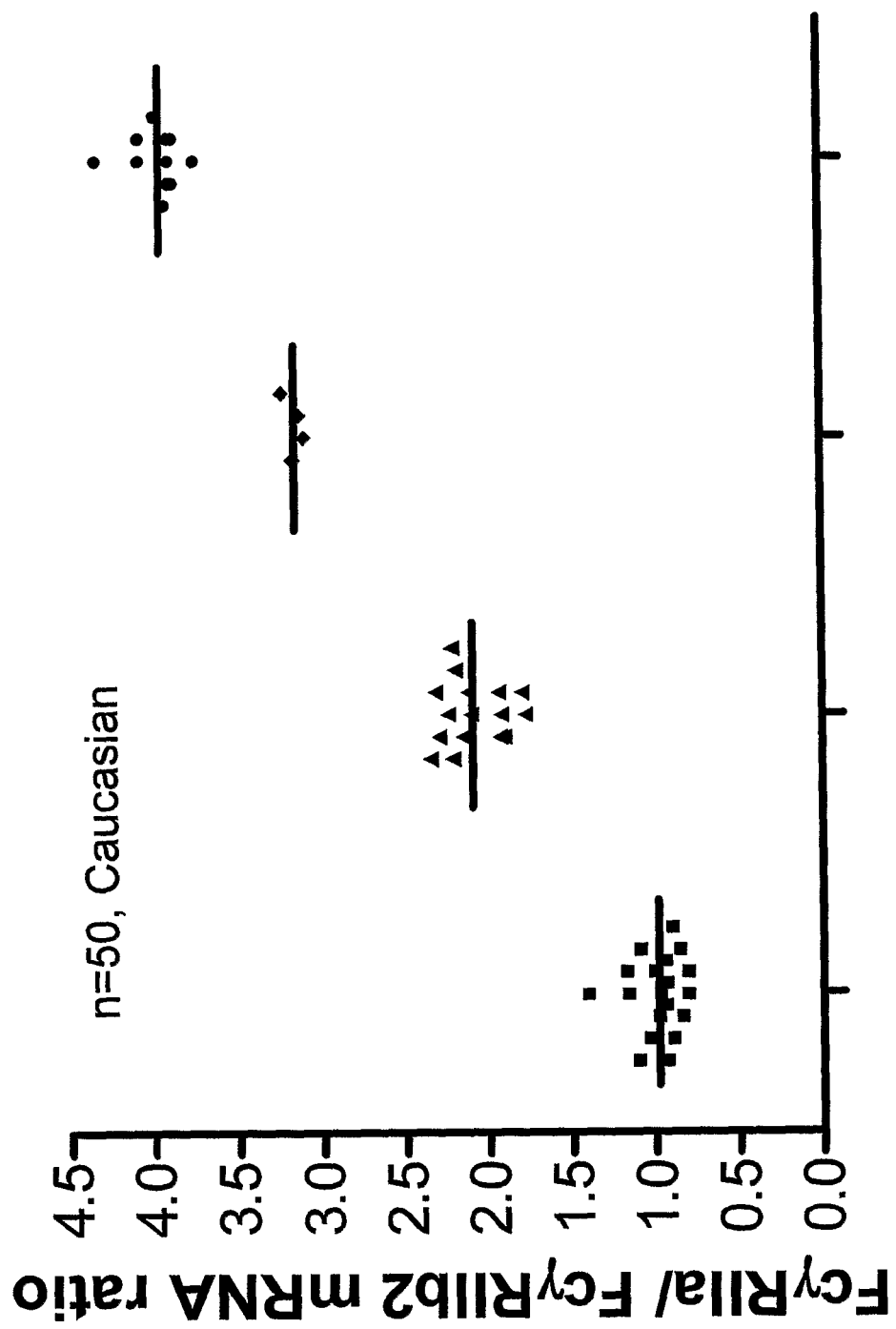

FIG. 2. Distribution of mRNA ratios of Fc-γRIIa and Fc-γRIIb in fifty healthy Caucasian individuals.

FIG. 3: FcγRIIc expression and function.

A. Distribution of FcγRIIc mRNA expression on leucocytes.

B. FcγRII expression on NK cells is limited to the FCGR2C-ORF genotype. Blood cells were incubated with CD56 and CD32. Lymphocytes were gated on basis of their forward scatter/side scatter pattern. NK cell population was determined as CD56-positive lymphocytes.

C. FcγRIIc expression on NK cells is modulated by IL-15 but not by IL-2. PBMCs were isolated and cultured. Expression on CD56+ NK cells was measured by flow cytometry with CD32 at the indicated time-points. There was a significant higher expression on day 2 and 5 on the IL-15 stimulated NK cells (p=0.01, n=5)

D. FcγRIIc mRNA is strongly upregulated by GM-CSF on cells of FCGR2C-ORF donors. Neutrophils and PBMCs were isolated and cultured for 4 hrs with the indicated stimuli. FcγRIIc mRNA was measured by quantitative RT-PCR. GM-CSF strongly upregulated FcγRIIc mRNA in neutrophils and to a lesser extent in PBMCs of FCGR2C-ORF genotyped donors, but not in FCGR2C-Stop donors (p=0.0001 and p=0.01, respectively; n=5-8).

E. rADCC. PBL were isolated and FcγRIIc functionality was assessed by rADCC. Cells from both FCGR2C-Stop and FCGR2C-ORF genotyped donors killed anti-FcγRIII-coated targets with similar kinetics (upper left and lower left panels, respectively). In contrast, only cells from FCGR2C-ORF genotyped donors were capable of killing anti-FcγRII coated targets (right lower panel) (n=4).

F. rADCC with stimulated cells. PBL were obtained and subsequently cultured for 2 days with or without IL-2 or IL-15. Thereafter, the cells were harvested and used in a rADCC. Cells from both FCGR2C-Stop and FCGR2C-ORF genotyped donors killed anti-FcγRIII-coated targets (left panel). In both cases IL-15 and to a lesser extent IL-2, enhanced specific lysis of the anti-FcγRIII-coated targets (n=3). In contrast, only cells from FCGR2C-ORF genotyped donors were capable of killing anti-FcγRII coated targets (right panel). Here, again IL-15 strongly enhanced the specific cell lysis (n=3).

EXAMPLES

Example 1

Validation CYBB Gene as Reference Gene

Primer Sequences:

| | | | |
|---|---|---|---|
| Albumin | Alb-F primer | 5'-TGAAACATACGTTCCCAAAGAGTTT-3' | (SEQ ID NO: 1) |
| | Alb-R primer | 5'-CTCTCCTTCTCAGAAAGTGTGCATAT-3' | (SEQ ID NO: 2) |
| FCGR2B | FCGR2Bex3-(Eco I)-F | 5'-CTCTCAAGCTCCTTGGGCTTCCTCTTCT-3' | (SEQ ID NO: 3) |
| | FCGR2Bex3-(Not I)-R | 5'-ACCCCCCTTTCCTGCAAACCTCTGC-3' | (SEQ ID NO: 4) |
| Y-chrom | SRY 109F | 5'-TGGCGATTAAGTCAAATTCGC-3' | (SEQ ID NO: 5) |
| | SRY 245R | 5'-CCCCCTAGTACCCTGACAATGTATT-3' | (SEQ ID NO: 6) |
| CYBB | CYBBex8-(HindIII)-F | 5'-GAGATCAAGCTTATGTCAAATATTTAAGCAAGCCTAC-3' | (SEQ ID NO: 7) |
| | CYBBex8-(XhoI)-R | 5'-GAGATCCTCGAGACTTGTCCATGATATAGTTAGACAC-3' | (SEQ ID NO: 8) |

FCGR2B/ALB Construct

To quantify the FCGR2B copy number with quantitative RT-PCR, a construct was made containing an 80-bp fragment of the ALB gene and 400-bp fragment of FCGR2B by Baseclear Labservices BV. For detailed protocol we refer to Base-Clear Labservices B.V, project code 11926.

In brief, a PCR was performed on a human DNA sample to obtain a PCR product of the ALB gene fragment using primers Alb-F and Alb-R, and primer pair FCGR2B-ex3-F and FCGR2B-ex3-R to obtain the FCGR2B exon 3 fragment. PCR products were blunted and phosphorylated (one of the products). Products were ligated overnight and a PCR was set up (on the ligation product) in order to amplify the total 480-bp fragment. PCR products were cloned into a pGEMT-easy vector, clones were picked and sequenced to confirm the sequence.

FCGR2B/CYBB Construct

Because a variation in the ALB gene copy number was observed, a new construct was made with CYBB as a reference/calibrator gene. The construct is based on a plasmid containing a 217-bp fragment of the CYBB gene and the 400-bp fragment of the FCGR2B gene. For this construct a Bluescript SK +/−phagemid was used. Using a standard cloning protocol, the CYBB fragment was cloned into the Bluescript SK +/−phagemid using the restriction enzymes HindIII and XhoI. Clones were picked and sequenced to confirm the inserted CYBB sequence. Subsequently the FCGR2B fragment was cloned in by using restriction enzymes EcoRI and NotI. Again the clones were sequenced to confirm the inserted sequences. With the restriction enzyme ScaI the plasmid was made linear. The construct containing the CYBB fragment can also be used in combination with other target genes or fragments thereof (e.g. FCGR2A, FCGR2C).

Quantitative Real-Time PCR

Amplification by PCR was performed on a LightCycler instrument (Roche, Almere, The Netherlands), with software version 3.5. The reaction was performed with Lightcycler FastStart DNA Master$^{PLUS}$ SYBR Green I (Roche). The annealing temperature for the ALB and FCGR2B primers was 65° C., for the CYBB primers 60° C. The reaction mixture consisted of 4 µl of the plasmid or 4 µl (100 ng) of genomic DNA, 1 µl of the forward and 1 µl of the reverse primer (1 µM), 4 µl of LightCycler FastStart DNA Master-PLUS SYBR Green I mix (Roche) and 10 µl of water. The PCR starts with a pre-incubation step for 10 min at 95° C. followed by 40 cycles of denaturation of 5 s at 95° C., annealing of the primers at 60° C. or 65° C. depending on the primers used for 30 s, followed by extension at 72° C. for 15 s. At the end of 40 cycles, a melting curve was generated to determine the specificity of the amplified products. Either a 10-fold serial dilution of the construct containing the FCGR2B/ALB or the construct containing the FCGR2B/CYBB (1:1) was used to construct a standard curve to which each sample was quantified. The threshold cycle (Ct) values of the serial diluted construct samples, determined by the 'second derivative maximum method' were used to calculate and plot a linear regression curve, as performed by the software. From this regression, the quality of the standard curve can be evaluated by the slope and correlation coefficient (r). The slope of the curve was used to calculate the efficiency of the PCR reaction (E). The E from the different PCR primer combinations did not differ more than 0.05. The 4 points of the standard curve were assigned a dimensionless quantity of 1000, 100, 10 and 1, respectively. Subsequently, the software can assign a dimensionless quantity to the unknown samples depending on their observed Ct value. Unknown samples were run in duplicate. For each sample the calculated value, depending on the Ct value, of the FCGR2B was divided by the value calculated for the reference/calibrator gene used in the assay (either albumin or CYBB).

The construct containing CYBB as a reference/calibrator gene was also used to make the following constructs: FCGR2A/CYBB, FCGR2C/CYBB.

Example 2

Copy Number Determination in Autoimmune Disease Patients Using Lightcycler Technology Using the method described in example 1, 40 Kawasaki Disease (KD) patients and 40 age-matched healthy controls were analyzed. In 17 KD patients a loss of copy number FCGR2B was observed, whereas this was only observed in 8 controls ($p<0.05$).

Example 3

Quantitative Reverse Transcriptase PCR for the Quantification of Transcripts mRNA was isolated from $10^7$ purified neutrophils and reverse transcribed into cDNA. Intron-spanning primers were designed to specifically amplify cDNA and exclude amplification of genomic DNA, yielding products of 100 bp for P-glucuronidase (GUS), 244 bp for FcγRIIa and 243 bp for FcγRIIb2.

Primer sequences:

```
β-glucuronidase:  fw primer:  5'-GAAAATATGTGGTTGGAGAGCTCATT-3', (SEQ ID NO: 9)
(GUS)             rev primer: 5'-CCGAGTGAAGATCCCCTTTTTA-3'.     (SEQ ID NO: 10)

FcγRIIa:          fw primer:  5'-ATCATTGTGGCTGTGGTCATTGC-3',    (SEQ ID NO: 11)
                  rev primer: 5'-TCAGGTAGATGTTTTTATCATCG-3'.    (SEQ ID NO: 12)

FcγRIIb2:         fw primer:  5'-GGAAAAAGCGCATTTGAGCCAATC-3',   (SEQ ID NO: 13)
                  rev primer: 5'-GGAAATACGAGATCTTCCCTCTCTG-3'.  (SEQ ID NO: 14)
```

When the FCGR2B/ALB construct was used for the standard curve, an observed outcome of an unknown sample (FCGR2B amount/ALB amount) of 1 means the individual is carrying equal amounts of copy number FCGR2B compared to ALB (thus far generally believed to be 2 copies). As CYBB is an X-linked gene, when the FCGR2B/CYBB construct is used, the interpretation of the outcome depends on the analyzed DNA being from a male or a female individual.

Results

From the first obtained results using the FCGR2B/ALB construct it became clear that the ALB gene is not a good reference gene. Observed outcome values of unknown samples of for instance 0.25 would imply a copy number of 0.5 FCGR2B. The inventors hypothesized that this result can only be observed when an individual is carrying 1 copy of FCGR2B and 4 copies of the gene encoding albumin, or 2 copies of FCGR2B and 8 copies of ALB. To test this hypothesis a quantitative RT-PCR was set-up with primers specific for the Y-chromosome and the ALB gene. Serial 10-fold dilutions from DNA from a male were used to construct a standard curve. For a male the expected outcome would be 1 (amount product Y-chrom/amount product ALB, as comparable to the standard curve used). However for the above-mentioned sample an outcome of 0.5 was observed. Inventors concluded that this can only be explained by 4 copies of the gene for albumin. To test this hypothesis further, also a quantitative PCR was set-up with CYBB specific primers and ALB. Again a 10-fold serial dilution of a male was used to construct the standard curve. The result from this test confirmed the earlier observed outcomes. Therefore, the construct containing FCGR2B/ALB was no longer used and a new construct containing FCGR2B/CYBB was developed.

Polymerase Chain Reaction

Amplification by PCR was performed on a LightCycler instrument (Roche, Almere, The Netherlands), with software version 3.5. The reaction was performed with LightCycler FastStart DNA Master$^{PLUS}$ SYBR Green I (Roche), which has been optimized by the manufacturer such that $MgCl_2$ optimalisation is no longer needed. The annealing temperature used for all primers was 60° C. The reaction mixture consisted of 2 μl of cDNA, 1 mM of each primer combination and 4 μl of LightCycler FastStart DNA Master$^{PLUS}$ SYBR Green I mix (Roche) in a total volume of 20 μl. All cDNA amplified was compared to the standard within the same run and in every run the same standard was used, although there was very little variation in the standard between runs. For amplification the following LightCycler protocol was used. The chemical cleft of the Taq polymerase was removed by preincubation for 10 minutes at 95° C. to activate the Taq polymerase; the template was amplified for 40 cycles of denaturation of 5 seconds at 95° C., annealing of the primers at 60° C. for 30 seconds, followed by extension at 72° C. for 15 seconds. The amount of fluorescence was measured at the end of each cycle at 72° C. At the end of 40 cycles, a melting curve was generated to determine the unique features of the DNA amplified. To identify the product obtained, it was submitted to a 1%, w/v, agarose gel to determine the size. Subsequently, the band obtained was purified by means of GFX PCR DNA and Gel Band purification kit (Amersham Biosciences) according to the manufacturer's instructions to remove excess of dNTP's and primers. The product was sequenced by Big-dye Terminator Cycle Sequencing (version 1.1) and ABI Prism software (Applied Biosystems, Foster City, Calif., USA). The sequence obtained was verified with BLAST (http://www.ncbi.nlm.nih.gov/BLAST/) to determine specificity. All products obtained were unique and had no overlap with other isoforms.

Standard Curves and Relative Quantitation

As a source of cDNA for standard curves to which all samples were normalized, neutrophils were isolated from an apheresis buffy coat obtained from the bloodbank North-West (Sanquin). Serial 10-fold dilutions from the cDNA obtained were made to which each sample was quantified with the method described in Technical Note No. LC 13/2001 (Roche Applied Science). In short, the threshold cycle ($C_T$) values, determined by the LightCycler software, were used to calculate and plot a linear regression curve, as performed by the software. From this regression, the quality of the standard curve can be evaluated by the slope and the correlation coefficient (r). The slope of the line was used to determine the efficiency of the reaction (E). From the $C_T$'S and the efficiencies obtained, the normalized ratio can be calculated with the following formula: $E_T^{CpT(C)-CpT(S)}:E_R^{CpR(C)-CpR(S)}$. In which $E_T$ is the efficiency of the PCR of the target gene; ER the efficiency of the PCR of the reference gene; CpT(C) is the measured $C_T$ of the target gene determined for standard or calibrator; CpT(S) is the measured $C_T$ of the target gene determined for the sample; CpR(C) is the measured $C_T$ of the reference gene of the calibrator or standard; and CpR(S) is the measured $C_T$ of the reference gene of the sample.

Validation of Quantitative RT-PCR for FcγRII Isoforms on the LightCycler

To study the expression levels of FcγRII isoforms on neutrophils, we set up a relative quantitative RT-PCR by means of the LightCycler instrument. This technique yielded a highly sensitive and specific method to determine FcγRIIa and FcγRIIb2 mRNA expression levels in neutrophils. The slopes of the standards for each PCR reaction were around −3.3, yielding an efficiency of about 2, indicating that during each cycle the specific product was doubled. Furthermore, each set of primers used resulted in a specific melting curve with its own melting temperature (Tm), whereas the non-template controls displayed a different melting curve or no product at all. FIG. 2 shows that distinct neutrophil mRNA ratios for FcγRIIa:FcγRIIb were found in a normal Caucasian population.

Example 4

MLPA Assay with Newly Developed Probes

Figure 1A:
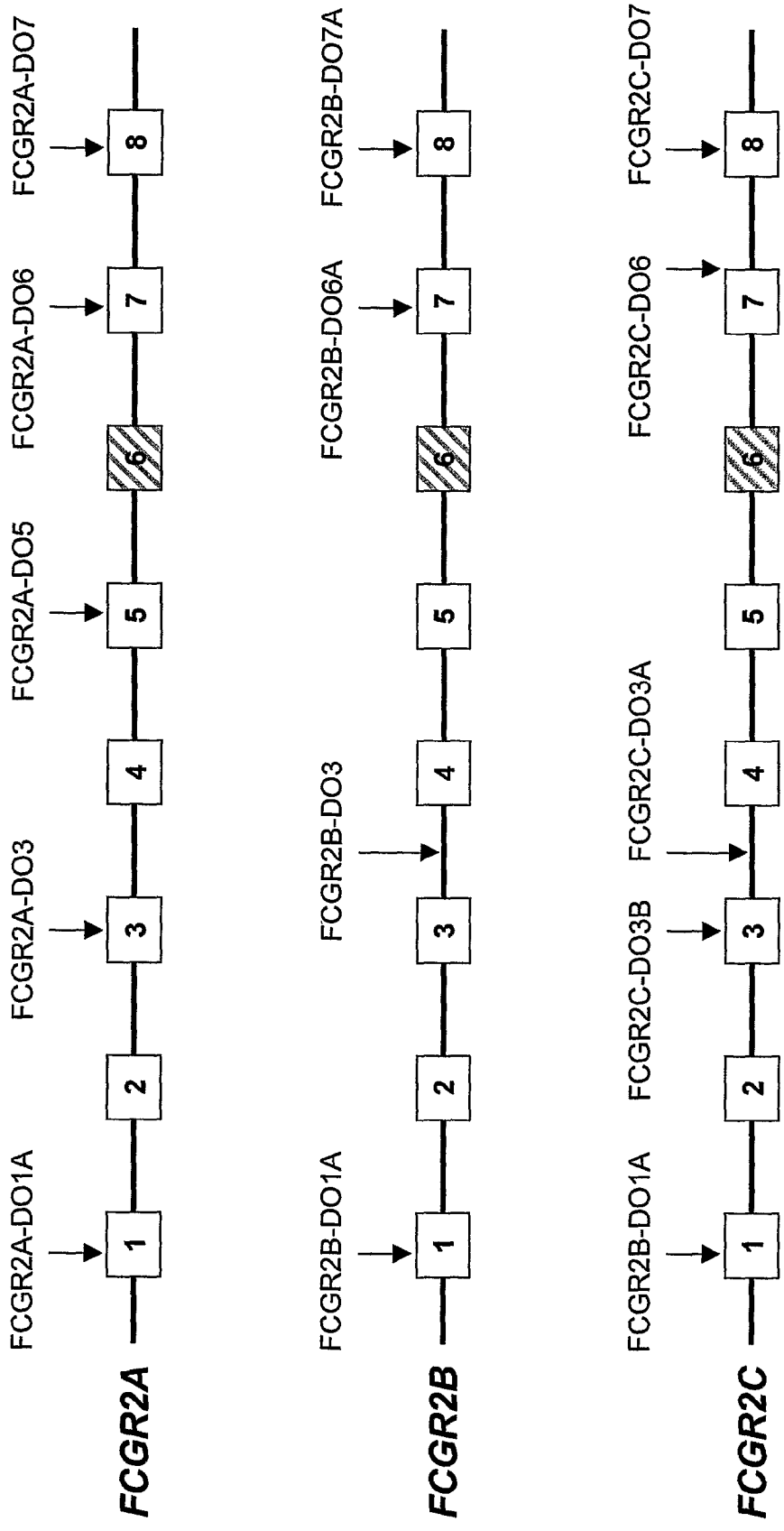
FIG. 1: Location of MLPA probes within the FCGR2 gene cluster (panel A) and the FCGR3 gene cluster (panel B).
Figure 1B:
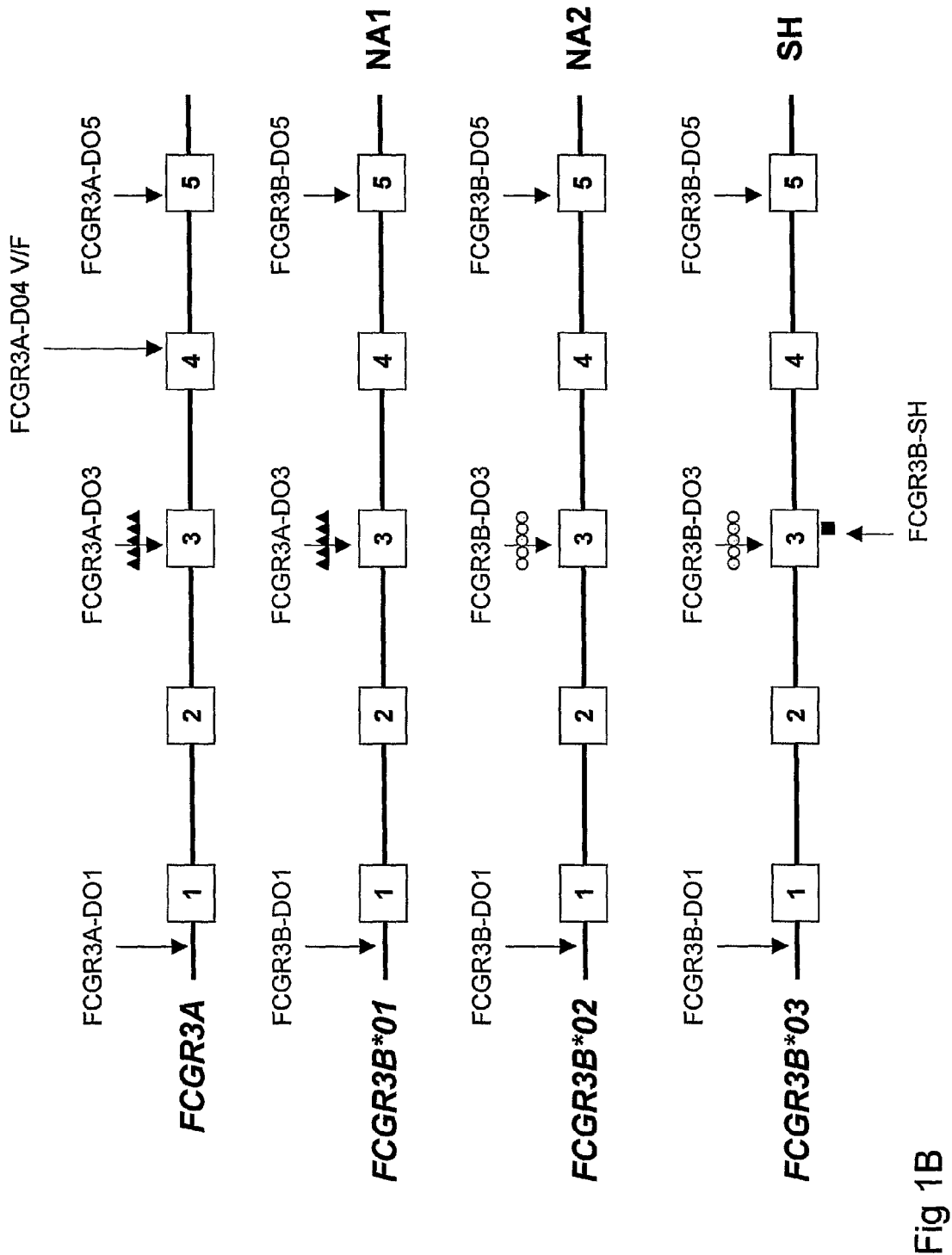

DNA was isolated with either the Puregene DNA isolation kit (Biozym, Hess, Oldendorf, Germany) or the QIAamp DNA Blood kit (Qiagen, Hilden, Germany). To analyse the FCGR gene cluster a Multiplex Ligation Probe Amplification assay is used. New probes were designed that are highly specific for the FCGR2A, FCGR2B, FCGR2C, FCGR3A and FCGR3B genes. As the FCGR gene cluster is very homologous, this was not possible for all sites. At least 3 probes per gene were designed to cover every single gene. In this way CNPs and partial insertion/deletions can be studied. Separate probes were designed to study known (functional) SNPs in FCGR2A (131 H/R), FCGR2B (232 I/T), promotor of FCGR2B and C (−386, −120), FCGR3A (NA1/NA2/SH) and FCGR3B (158 V/F). For an overview of the location and the specific target sequences of the probes see FIGS. 1A and 1B and Table 2 below. Probes were manufactured according to Schouten et al., 2002. Because of the homology between certain probes, probes have to be divided over two separate mixes (probe MIX 1 and probe MIX 2; see tables 2A and 2B, respectively) to prevent competition.

TABLE 2A

"Probe MIX 1".

| Length | Probe # | Gene/Chr. position | Comments |
|---|---|---|---|
| 130 | 0797-L0463 | Control probe, Chr. 5q31 | |
| 136 | 2271-L2327 | Control probe, Chr. 1p36 | |
| 142 | 3605-L2972 | FCGR2A, exon 1 (D01A) | |
| 148 | 3610-L2977 | FCGR2C, exon 7 (D07) | |
| 154 | 2679-L2144 | Control probe, Chr. 1q25 | |
| 160 | 3616-L2983 | FCGR3A, exon 3 (D03) | SNP detects NA1 variant and FCGR3A |
| 172 | 2677-L2143 | Control probe, Chr. 1q25 | |
| 181 | 3611-L2978 | FCGR2B, exon 1 (D01A) | Detects also FCGR2C |
| 193 | 3606-L2973 | FCGR2A, exon 1 (D01B) | |
| 202 | 4812-L4198 | FCGR2B, 232I/T (D05B) | SNP detects the frequent 232-I variant |
| 211 | 3609-L2976 | FCGR2C, exon 6 (D06) | |
| 220 | 3619-L2986 | FCGR2B, intron 3 (D03) | At intron/exon boundary of exon 4 |
| 229 | 1487-L1095 | Control probe, Chr. 16q24 | |
| 238 | 0974-L0561 | Control probe, Chr. 14q12 | |
| 265 | 1325-L0874 | Control probe, Chr. 17p13 | |
| 274 | 3613-L2980 | FCGR2B, exon 6 (D06A) | |
| 283 | 3608-L2975 | FCGR2A, exon 5 (D05A) | |
| 292 | 3162-L2603 | Control probe, Chr. 11p11 | |
| 301 | 1916-L1460 | Control probe, Chr. 1q21 | |
| 310 | 3618-L2985 | FCGR3B, exon 5 (D05) | |
| 319 | 3612-L2979 | FCGR2B, exon 7 (D07A) | |
| 328 | 1918-L1462 | Control probe, Chr. 1q21 | |
| 337 | 3614-L2981 | FCGR3A, exon 1 (D01) | |
| 346 | 3615-L2982 | FCGR3B, exon 1 (D01) | |
| 355 | 4813-L4187 | FCGR2A, 131H/R (D04A) | SNP detects 131-H variant |
| 373 | 2560-L2023 | Control probe, Chr. 3q23 | |
| 382 | 2908-L2302 | Control probe, Chr. Xq23 | |
| 391 | 4816-L4190 | FCGR3A, 158V/F (D04) | SNP detects 158-F variant |
| 400 | 4818-L4192 | FCGR2C, 2C-STOP-specific | |

Probes in bold indicate those which are required for a reliable assay outcome. Target sequences of the probes are presented in Tables 2C, D and E.

TABLE 2B

"Probe MIX 2".

| Length | Probe # | Gene/Chr. position | Comments |
|---|---|---|---|
| 130 | 0797-L0463 | Control probe, Chr. 5q31 | |
| 136 | 2271-L2327 | Control probe, Chr. 1p36 | |
| 142 | 4817-L4191 | FCGR2B, exon 3 (D03B) | Detects FCGR2B and FCGR2C-ORF |
| 148 | 3610-L2989 | FCGR2A, exon 7 (D07) | |
| 154 | 2679-L2144 | Control probe, Chr. 1q25 | |
| 165 | 3616-L2990 | FCGR3B exon 3 (D03) | SNP detects NA2 variant |
| 172 | 2677-L2143 | Control probe, Chr. 1q25 | |
| 181 | 3611-L2978 | FCGR2B, exon 1 (D01A) | Detects FCGR2B and FCGR2C |
| 202 | 4812-L4186 | FCGR2B, 232I/T (D05B) | SNP detects rare 232-T variant |
| 211 | 4815-L4189 | FCGR2A, exon 6 (D06B) | |
| 220 | 3619-L2994 | FCGR2C, intron 3 (D03) | At intron/exon boundary of exon 4 |
| 229 | 1487-L1095 | Control probe, Chr. 16q24 | |
| 238 | 0974-L0561 | Control probe, Chr. 14q12 | |
| 247 | 4821-L4195 | FCGR2A, exon 3 (D03C) | |
| 265 | 1325-L0874 | Control probe, Chr. 17p13 | |
| 274 | 3613-L2980 | FCGR2B, exon 6 (D06A) | |
| 283 | 4819-L4193 | FCGR3B, SH (D03SH) | SNP FCGR3*3 (SH) variant |
| 292 | 3162-L2603 | Control probe, Chr. 11p11 | |
| 301 | 1916-L1460 | Control probe, Chr. 1q21 | |
| 310 | 3618-L2993 | FCGR3A, exon 5 (D03) | |
| 319 | 3612-L2979 | FCGR2B, exon 7 (D07A) | |
| 328 | 1918-L1462 | Control probe, Chr. 1q21 | |
| 355 | 4814-L4188 | FCGR2A, 131 H/R (D04B) | SNP detects 131-R variant |
| 373 | 2560-L2023 | Control probe, Chr. 3q23 | |
| 382 | 2908-L2302 | Control probe, Chr. Xq23 | |
| 391 | 4816-L4196 | FCGR3A, 158V/F (D04) | SNP detects 158-V variant and FCGR3B |

Probes in bold indicate those which are required for a reliable assay outcome. Target sequences of the probes are presented in Tables 2C, D and E.

TABLE 2C

Sequence information of FCGR2 probes used

| Length Mix1 | Mix2 | Probe # | Gene # | Sequence detected |
|---|---|---|---|---|
| 142 | | 3605-L2972 | FCGR2A-D01A | GTCTCAGAATGTATGTCCCAGAAACCTGTGGCTGCTTCAA (SEQ ID NO: 15) |
| | 193 | 3606-L2973 | FCGR2A-D01B | ATAGTCATCCCAGCACTGTGCCAACGTCCAGTGGGTTTTA (SEQ ID NO: 16) |
| | 247 | 4821-L4195 | FCGR2A-D03C | TCTGTGACTCTGACATGCCAGGGGGCTCGCAGCCCTGAGA (SEQ ID NO: 17) |
| 355 | | 4813-L4187 | FCGR2A-D04A | AAATCCCAGAAATTCTCCCATTTGGATCCCACCTTCTCCAT (SEQ ID NO: 18) |
| | 355 | 4814-L4188 | FCGR2A-D04B | GGAGAAGGTGGGATCCAAACGGGAGAATTTCTGGGATTTT (SEQ ID NO: 19) |
| 283 | | 3608-L2975 | FCGR2A-D05A | TCATTGCGACTGCTGTAGCAGCCATTGTTGCTGCTGTAGT (SEQ ID NO: 20) |
| | 211 | 4815-L4189 | FCGR2A-D06B | AGATGGCTGGGATTACTCACCTCAAATTGGGCAGCCTTCA (SEQ ID NO: 21) |
| | 181 | 3611-L2978 | FCGR2B-D01A | ATAGCACAGCTGTCCACAGAAGCATATGACCCCAAGGCTG (SEQ ID NO: 22) |
| 220 | | 3619-L2986 | FCGR2B-D03 | CTGAAAGACACAAAAAACCGCAGAGGACCCGGGAGGTCTT (SEQ ID NO: 23) |
| | 220 | 3619-L2994 | FCGR2B-D03 | GTGAAAGACACAGAAAACCCAGAGGACCCGGGAGGTCTT (SEQ ID NO: 24) |
| | 142 | 4817-L4191 | FCGR2B-D03B | GGCAGAGAGAGGAGGTAGCATGAAGAAGAGGAAGCCCAGG (SEQ ID NO: 25) |
| | 202 | 4812-L4186 | FCGR2B-D05B-C | GTGGCTGTGGTCACTGGGACTGCTGTAGCGGCCATTGTTG (SEQ ID NO: 26) |

TABLE 2C-continued

Sequence information of FCGR2 probes used

| Length Mix1 ... ... Mix2 | Probe # | Gene # | Sequence detected |
|---|---|---|---|
| 202 | 4812-L4198 | FCGR2B-D05B-T | GTGGCTGTGGTCACTGGGATTGCTGTAGCGGCCATTGTTG (SEQ ID NO: 27) |
| ... 274 | 3613-L2980 | FCGR2B-D06A | CAATCCCACTAATCCTGATGAGGCTGACAAAGTTGGGGTG (SEQ ID NO: 28) |
| ... 319 | 3612-L2979 | FCGR2B-D07A | CAATCACCTATTCACTTCTCATGCACCCGGATGCTCTGGA (SEQ ID NO: 29) |
| 211 | 3609-L2976 | FCGR2C-D06 | GAAGGCTGCCCAATTTGAGATGAGTAATCCCAGCCATCTC (SEQ ID NO: 30) |
| ... 148 | 3610-L2989 | FCGR2A-D07 | GCCATCAGAAAGAGACAACTTGAAGAAACCAACAATGACT (SEQ ID NO: 31) |
| 148 | 3610-L2977 | FCGR2C-D07 | GCCATCAGAAAGAGACAACCTGAAGAAACCAACAATGACT (SEQ ID NO: 32) |
| 400 | 4818-L4192 | FCGR2C-STOP | TTGGGCTTCCTCTTCCTCACGCTACCTCCTCTCTCTGCCC (SEQ ID NO: 33) |

TABLE 2D

Sequence information of FCGR3 probes used

| Length Mix1 ... ... Mix 2 | Probe # | Gene # | Sequence detected |
|---|---|---|---|
| 337 | 3614-L2981 | FCGR3A-D01 | TCCAGGCTCTTTCCTTCCTGGTCCTGTTCTATGGTGGGGC (SEQ ID NO: 34) |
| 160 | 3616-L2983 | FCGR3A-D03 | CTCAATGGTACAGGGTGCTCGAGAAGGACAGTGTGACTCT (SEQ ID NO: 35) |
| 391 | 4816-L4190 | FCGR3A-D04 | CTACTTCTGCAGGGGGCTTTTTGGGAGTAAAAATGTGTCT (SEQ ID NO: 36) |
| ... 391 | 4816-L4196 | FCGR3A-D04 | CTACTTCTGCAGGGGGCTTGTTGGGAGTAAAAATGTGTCT (SEQ ID NO: 37) |
| ... 310 | 3618-L2993 | FCGR3A-D05 | AGACTGGAAGGACCATAAATTTAAATGGAGAAAGGACCCT (SEQ ID NO: 38) |
| 346 | 3615-L2982 | FCGR3B-D01 | TCCACCCATCTCTGTCACCTGCCAGTTTCCTTTTCTTGAA (SEQ ID NO: 39) |
| ... 165 | 3616-L2990 | FCGR3B-D03 | CTCAATGGTACAGCGTGCTTGAGAAGGACAGTGTGACTCT (SEQ ID NO: 40) |
| 310 | 3618-L2985 | FCGR3B-D05 | AGACTGGAAGGACCATAAACTTAAATGGAGAAAGGACCCT (SEQ ID NO: 41) |

TABLE 2E

Sequence information of Control probes used

| Length Mix1 and Mix2 | Probe # | Gene/# | Sequence detected |
|---|---|---|---|
| 130 | 0797-L0463 | IL4-D01 | CACTGCAAATCGACACCTATTAATGGGTCTCACCTCCCAA (SEQ ID NO: 42) |
| 136 | 2271-L2327 | CAB45-D01 | CCACCAGGAGGTCTTCCTAGGCAAGGACCTGGGTGGCTTT (SEQ ID NO: 43) |
| 154 | 2679-L2144 | HRPT2-D11 | GAGGGTGCATCTGCCCGGAAGACTCAGACTCCTGCAGCCC (SEQ ID NO: 44) |

TABLE 2E-continued

Sequence information of Control probes used

| Length Mix1 and Mix2 | Probe # | Gene/# | Sequence detected |
|---|---|---|---|
| 229 | 14871-L1095 | FANCA-D15 | AAGAAGGCCCTGGTCTTCCTGTTTACGTTCTTGTCAGAAC (SEQ ID NO: 45) |
| 238 | 0974-L0561 | TINF2-D01 | GCGGACGCTGCGTGGAACATTTTCCGCGAGTACTGGAGTT (SEQ ID NO: 46) |
| 265 | 1325-L0874 | ASPA-D05 | GCCATTGAGGTCTATAAAATTATAGAGAAAGTTGATTACC (SEQ ID NO: 47) |
| 292 | 3162-L2603 | MNYBPC3-D29 | CGCTTCCGCATGTTCAGCAAGCAGGGAGTGTTGACTCTGG (SEQ ID NO: 48) |
| 301 | 1916-L1460 | LMNA-D02 | AGGGTGACCTGATAGCTGCTCAGGCTCGGCTGAAGGACCT (SEQ ID NO: 49) |
| 328 | 1918-L1462 | LMNA-D04 | AGACCCGACTGGTGGAGATTGACAATGGGAAGCAGAGTGA (SEQ ID NO: 50) |
| 373 | 2560-L2023 | ATR-D47 | AGACCCATGTTCTTGACATTGAGCAGCGACTACAAGGTGT (SEQ ID NO: 51) |
| 382 | 2908-L2302 | PAK3-D01 | GTAACAACCGGGATTCTTCAGCACTCAACCACAGCTCCAA (SEQ ID NO: 52) |

MLPA Assay

The MLPA assay was performed according to the instructions of the manufacturer (MLP Holland BV, Amsterdam, The Netherlands). In brief, 5 µl of DNA (20 ng/µl) is denatured at 98° C. for 5 min and then cooled to 25° C. in a thermal cycler with heated lid. 1.5 µl of probe mix and 1.5 µl of buffer is added to each sample and incubated for 1 min at 95° C. followed by 16 hr at 60° C. Then 32 µl of Ligase-65 mix is added to each sample while at 54° C., followed by an incubation of 15 min at 54° C. and 5 min at 98° C. This ligation mixture is diluted 4 times. 10 µl of polymerase mix is added containing one single primer pair. Directly after adding the polymerase mix the PCR reaction is started. PCR conditions are 36 cycles of 30 s 95° C., 30 s 60° C., 60 s 72° C. followed by 20 min at 72° C. Following the PCR reaction 1 µl of the PCR reaction is mixed with 0.5 µl CXR 60-400 (Promega) internal size standard and 8.5 µl of deionised formamide and incubated for 10 min at 90° C. Products are then separated by electrophoresis on an ABI-3100.

Data Analysis

Analysis of a limited number of samples can be done by visual examination of the capillary electrophoresis peak. For the analysis of large number of samples the program Genemarker (v 1.30) is suitably used. In brief, the capillary electrophoresis peak profiles are imported into the program and then signals are normalised for signal strength using the assigned control probes. As MLPA is a relative quantification manner one sample has to be assigned as reference sample. The normalized height (or the area) of the probe amplification product of the unknown sample is divided by the normalized height of that probe amplification product of the reference. A ratio between 0.8-1.2 is considered normal, below 0.8 is considered as loss in copy number and above 1.2 as gain of copy number.

Results on Kawasaki Disease Patients

SNPs; By conventional SNP PCR no significant differences can be detected in samples from 170 patients with Kawasaki disease (Biezeveld et al. Fc gamma Receptors in Kawasaki disease, The involvement of Fc gamma receptor gene polymorphisms in Kawasaki disease. Clin Exp Immunol. 2007; 147: 106-111). DNA of 70 known samples (used in a previous study with conventional PCR methods to genotype the SNPs in the FCGR gene cluster) were analysed with the MLPA assay to validate the probes identifying the SNPs. The only discrepancies observed were caused by the fact that with the conventional methods no absolute quantification is possible and therefore a sample with only 1 FCGR3B allele is typed as NA2/NA2 (homozygous) instead of NA2/null with the new MLPA method.

CNPs; DNA of 70 Kawasaki Disease (KD) patients and 100 healthy Caucasian controls was tested.

in 30 KD samples an altered FCGR2B exon-3 amplification product was observed, whereas this was observed in none of the control samples.

in 23 KD (32%) samples a FCGR2C-ORF (open reading frame in exon 3) resulting in an activating receptor was observed, compared to 18% in the healthy controls (p<0.05).

in 3 KD samples 3 copies of the complete FCGR3A gene were observed, not found in control samples.

in 3 KD samples and 2 controls samples 3 copies of the complete FCGR3B gene were observed without the SH-variant being present on one of the copies.

Results on ITP Patients

DNA of 116 samples of ITP patients were tested by the MLPA assay. Increased variation in the FCGR2 and FCGR3 gene clusters was found in Caucasian ITP patients as compared to healthy Caucasian controls (n=100).

In the FCGR2C gene a SNP in exon 3 converts a glutamine in the open reading frame (ORF) to the most commonly found stop codon. In the control group 82% of the individuals were homozygous $FCGR2C^{stop/stop}$. Whereas, the FCGR2C-ORF gene was present in 18% of healthy individuals, FCGR2C-ORF was found in 35% of the patients with the hematological autoimmune disease ITP (n=116; odds ratio (OR): 2.4, 95%-confidence interval (95% CI): 1.3-4.3; p=0.009). We have evidence that the FCGR2C-ORF gene translates into an activating IgG receptor on the cell membrane, exerting antibody-mediated activity such as antibody-dependent cellular cytotoxicity (ADCC) by immune cells.

Figure 3A:
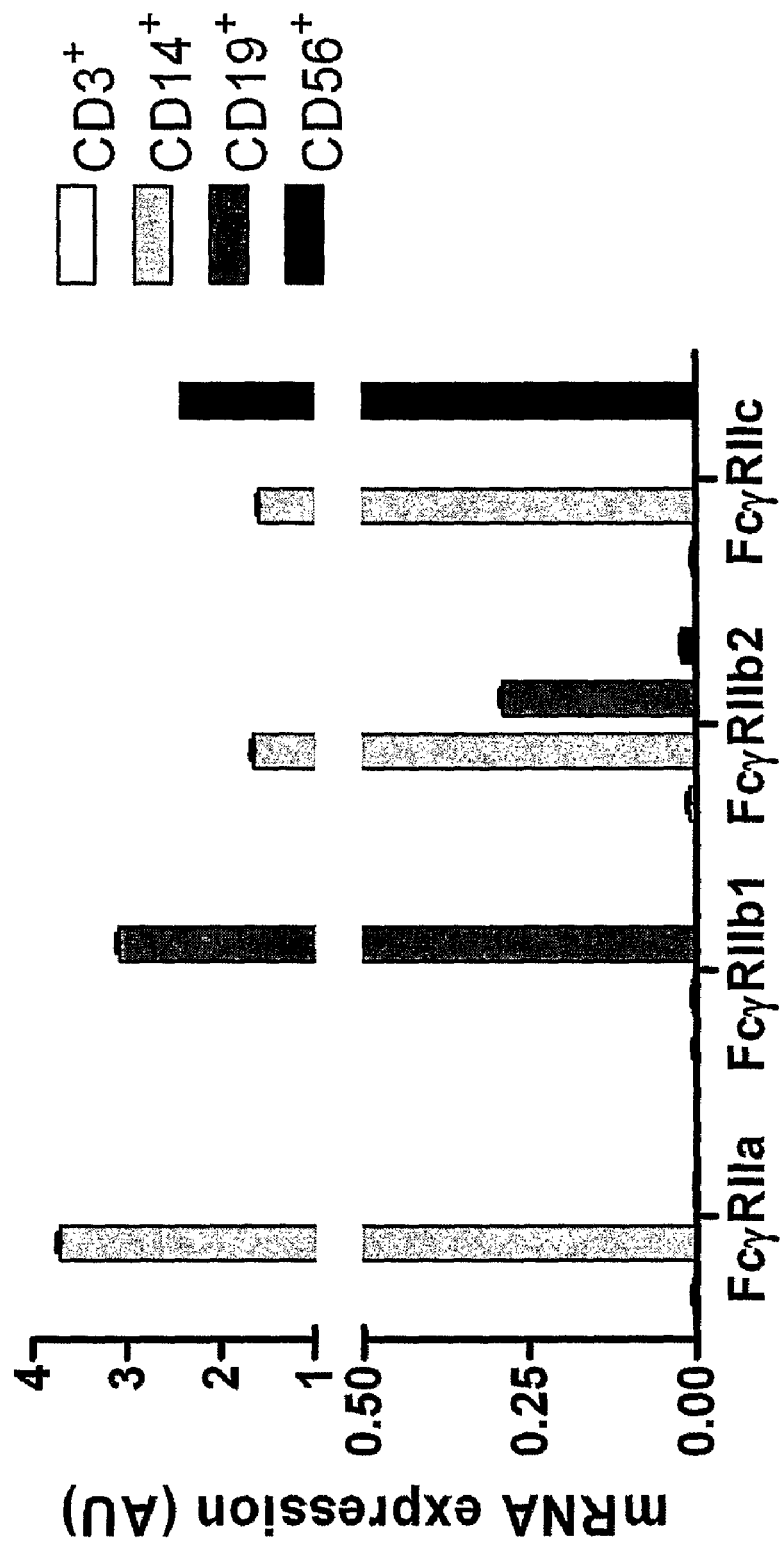
Figure 3B:
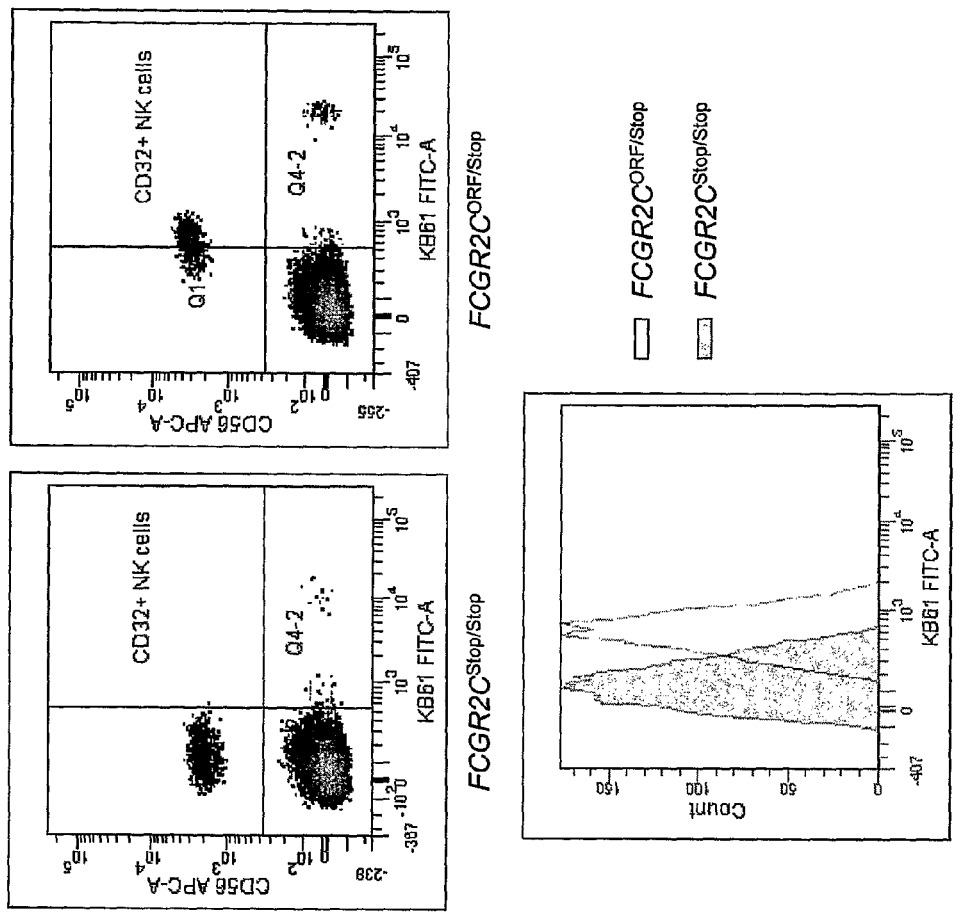

Also a significant difference in genotype (p=0.01) and allele (p=0.02) frequency for the promoter polymorphism −386G/C was observed. The genotype −386CC was rare, and only observed in an ITP patient.

the expression of FcγRIIc on NK cells of individuals with the FCGR2COR$^{stop/stop}$ genotype and the FCGR2C$^{stop/stop}$ genotype. It was found that the presence of an FCGR2C-ORF allele correlates with FcγRII expression on NK cells, whereas the absence of a functional allele corresponded with the absence of FcγRII on NK cells (FIG. 3B and Table 3). Thus, we conclude that FcγRIIc is present on NK cells.

TABLE 3

|  | expression | | MLPA | gene-specific PCR | | | |
| --- | --- | --- | --- | --- | --- | --- | --- |
| Sample | NK cells | MFI | FCGR2C stop/ORF | 2B/C-386 | 2B-386 | 2B-120 | 2C-386 | 2C-120 |
| 1 | no | nd | stop/stop | W | | | | |
| 2 | no | nd | stop/stop | W | | | | |
| 3 | no | nd | stop/stop | W | | | | |
| 4 | no | nd | stop/stop | W | | | | |
| 5 | no | nd | stop/stop | W | | | | |
| 6 | no | nd | stop/stop | W | | | | |
| 7 | no | nd | stop/stop | W | | | | |
| 8 | no | nd | stop/stop | W | | | | |
| 9 | no | nd | stop/stop | W | | | | |
| 10 | no | nd | stop/stop | W | | | | |
| 11 | yes | 590 | ORF/stop | He | GC | TA | GC | TT |
| 12 | yes | 1188 | ORF/stop | He | GC | TA | GC | TT |
| 13 | yes | 1648 | ORF/stop | He | GC | TA | GC | TT |
| 14 | yes | 2602 | ORF/stop | He | GC | TA | GC | TT |
| 15 | yes | 2123 | ORF/stop | He | GC | TA | GC | TT |
| 16 | yes | 1109 | ORF/stop | He | GC | TA | GC | TT |
| 17 | yes | 2380 | ORF/stop | He | GC | TA | GC | TT |
| 18 | yes | 1243 | ORF/stop | He | GC | TA | GC | TT |
| 19 | yes | 1394 | ORF/stop | He | CC | AA | GC | TT |
| 20 | yes | 1629 | ORF/stop | He | GC | TA | GC | TT |

In the same series of DNA samples, we confirmed the previously observed overrepresentation of the SNP in FCGR3A encoding the FcγRIIIa-158V variant, being most prevalent in ITP of childhood-onset (p=0.0005) and not in ITP of adult-onset (p=0.3).

FCGR2C Splice Variants.

To date, five splice variants of FcγRIIc have been reported, two of which result in a membrane-anchored receptor, i.e. FcγRIIc1 encoded by the full transcript, and FcγRIIc3 reported to lack exon 7. We hypothesized that alternative splicing of the FcγRIIc transcript is restricted to the FCGR2C-stop allele. To investigate this, we cloned the FcγRIIc transcripts from a single individual with an FCGR2C$^{ORF/ORF}$ genotype and three individuals with an FCGR2C$^{ORF/stop}$ genotype into a bacterial expression vector and obtained the sequence of at least 20 clones per individual. Upon sequencing of all these clones it was found that individuals genotyped as FCGR2C$^{ORF/ORF}$ or FCGR2C$^{ORF/stop}$ only express FcγRIIc1 (data not shown).

Distribution of FCGR2C Expression.

Next, mRNA expression of FcγRII isoforms in neutrophils, monocytes, NK cells, T cells and B cells from healthy volunteers was investigated. Transcripts for FcγRIIa, FcγRIIb2 and FcγRIIc, but not FcγRIIb1, were found in both neutrophils and monocytes while B cells only contained FcγRIIb1 (FcγRIIb1 contains exon 6 of FCGR2B, FcγRIIb2 does not contain this exon). T cells did not express any of the FcγRII isoforms, whereas. NK cells solely expressed FcγRIIc.

Expression of FcγRIIc on NK Cells.

FCGR2A, FCGR2B and FCGR2C have 92-96% sequence homology. There are no monoclonal antibodies available that can truly distinguish between FcγRIIa, FcγRIIb and FcγRIIc, rendering it difficult to quantify the protein expression on cells. However, we found that NK cells only expressed mRNA of the FcγRIIc isoform. For this reason, we examined In Vitro Activation of NK Cells.

Figure 3C:
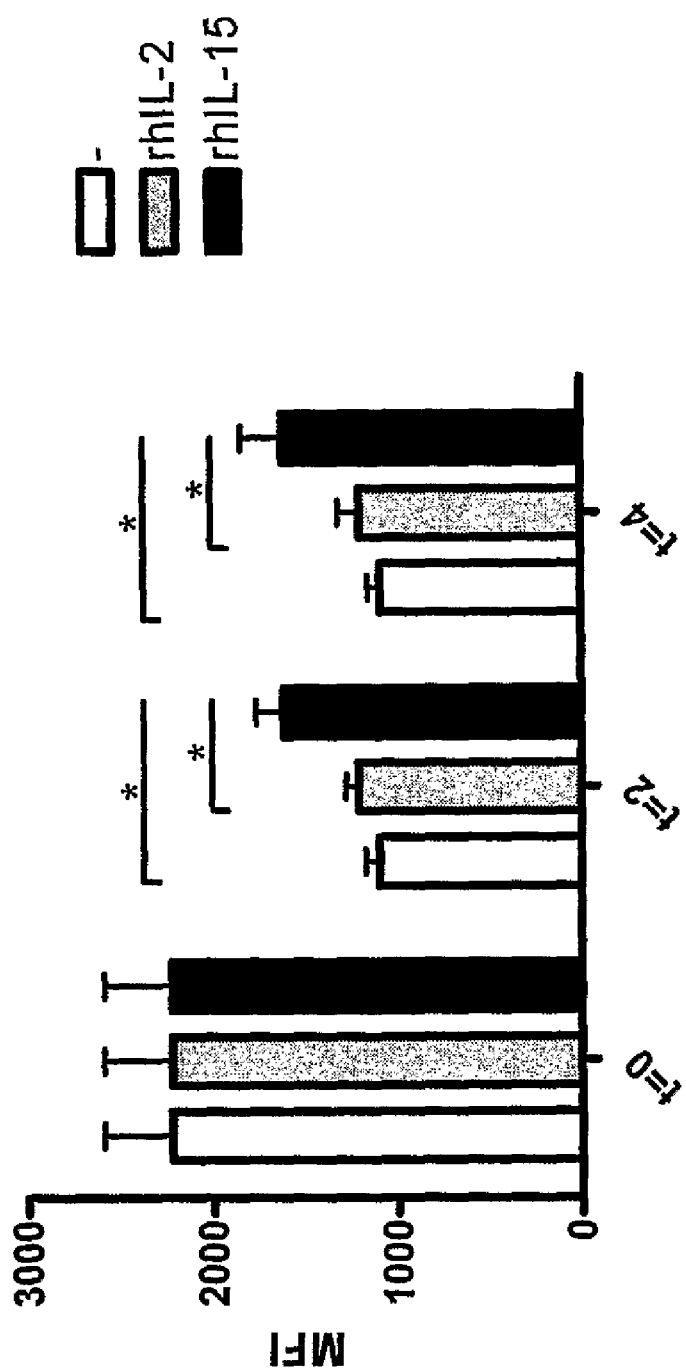
Figure 3D:
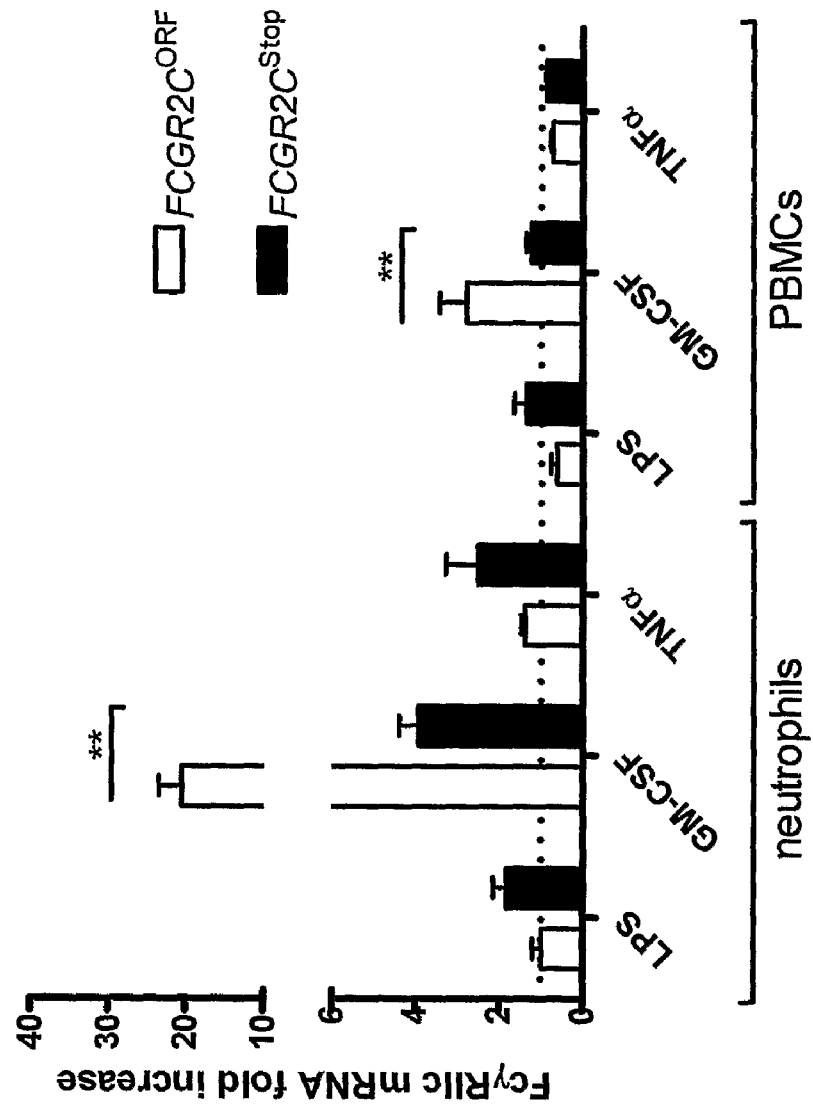

The FcγRIIc expression on NK cells was measured 3 times at various time intervals (range 2-5 months) in four individuals with the FCGR2C$^{ORF/stop}$ genotype. Minor fluctuation was observed over time (MFI±SEM: 1707±211). Subsequent testing in NK cell cultures with the NK cell activators IL-2 or IL-15 showed the ability to modulate the FcγR expression on NK cells. We found that both IL-2 and IL-15 upregulated the surface expression of FcγRIIIa on NK cells. In contrast, FcγRIIc expression was downregulated during culture, although IL-15 significantly rescued the loss of FcγRIIc expression compared to either IL-2 or medium (FIG. 3C).

Because surface expression of FcγRIIc on neutrophils and monocytes can at present not be monitored owing to the lack of specific antibodies, the regulation of FcγRIIc mRNA in these cells was tested after incubating neutrophils as well as PBMCs with the inflammatory activators LPS, GM-CSF or TNFα. In particular, GM-CSF induced a strong upregulation of FcγRIIc mRNA in neutrophils obtained from individuals with an FCGR2C$^{ORF/stop}$ genotype, whereas this was found to a significantly lower extent in individuals with an FCGR2C$^{stop/stop}$ genotype (p<0.01, FIG. 3D).

Redirected Antibody-Dependent Cellular Cytotoxicity.

To assess whether FcγRIIc expression on the innate immune cells was functionally active, we tested the capability of the NK cells to kill antibody-coated targets. In order to selectively target either FcγRIIc or FcγRIIIa on NK cells, the rADCC test was employed, involving the FcγR-bearing murine mastocytoma P815 cell line loaded with anti-FcγRII or anti-FcγRIII antibody.

Figure 3E:
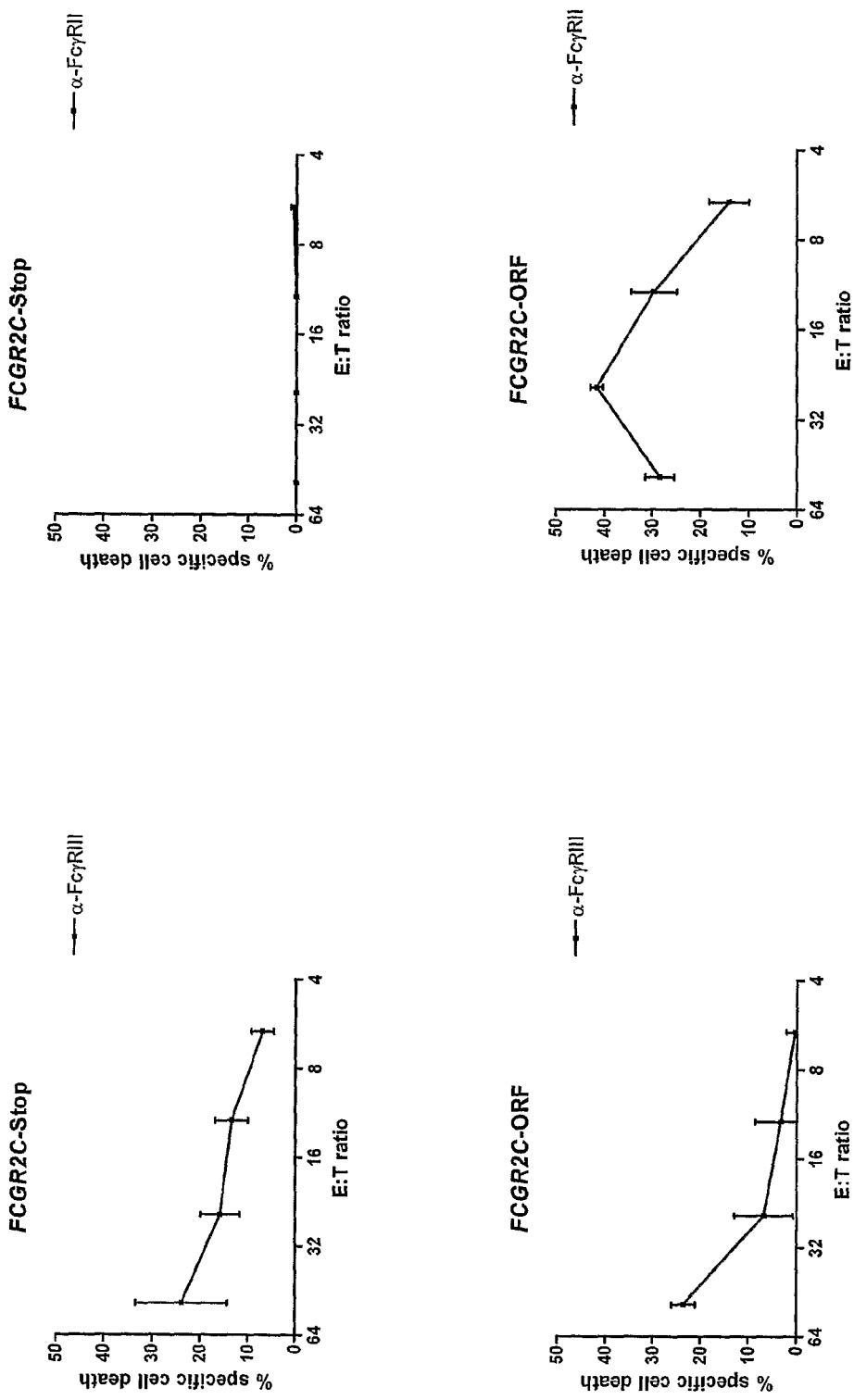
Figure 3F:
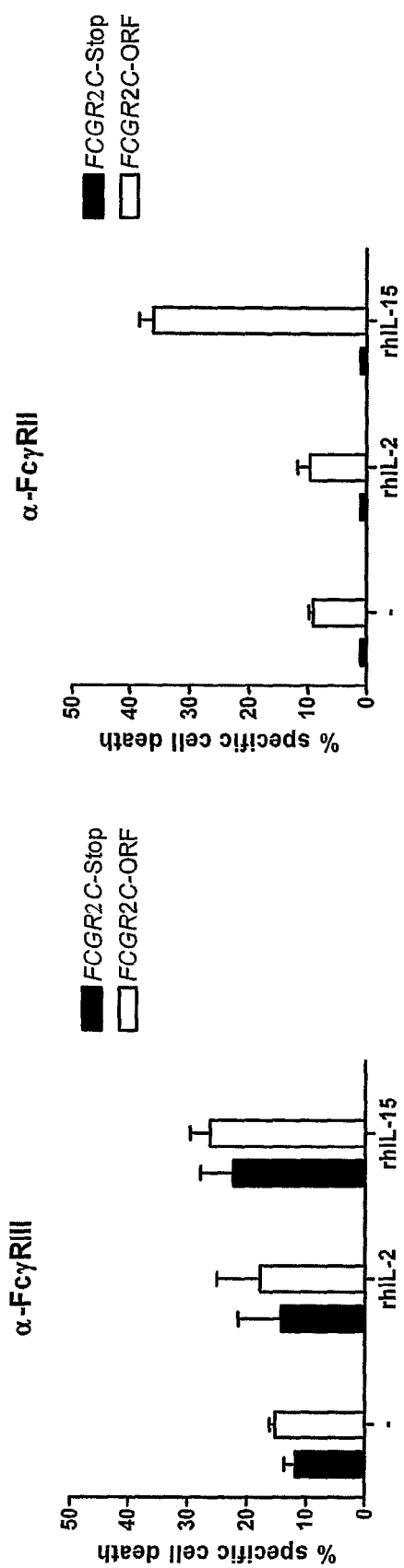

NK cells of an FCGR2C$^{ORF/stop}$ genotype donor killed both anti-FcγRII and anti-FcγRIII-loaded target cells (FIG. 3E). In contrast, NK cells of an FCGR2C$^{stop/stop}$ genotype donor were only able to kill anti-FcγRIII-loaded target cells. When the expression of FcγRIIc was reduced by culturing NK cells in the presence of activating cytokines, the effect of FcγRIIc crosslinking in the rADCC assay showed even more pronounced killing capacity in IL-2 or IL-15-activated NK cells (FIG. 3F).

In conclusion, these data show that FCGR2C-ORF predisposes to ITP. We have shown that FcγRIIc is expressed by phagocytes and NK cells, and that this enhances effector functions towards antibody-coated targets. Furthermore, we have shown that under inflammatory conditions (GM-CSF or IL-15), FcγRIIc function is even further enhanced. Thus, taken together, these results show that FCGR2C is a variably expressed gene highly relevant for immunity, and that it can serve as prognostic and diagnostic marker to assess susceptibility and severity of infections and autoimmune disease.

INCORPORATION OF SEQUENCE LISTING

Incorporated herein by reference in its entirety is the Sequence Listing for the application. The Sequence Listing is disclosed on a computer-readable ASCII text file titled, "sequence.txt", created on Feb. 23, 2009. The sequence.txt file is 11 kb in size.

The invention claimed is:

1. A set of probes for multiplex ligation probe amplification (MLPA) analysis of the FcγRII/FcγRIII gene cluster, the set comprising assay probes consisting of 130-480 nucleotides wherein the assay probes have the sequences set forth in SEQ ID NOs: 15, 16, 18, 20, 22, 23, 27-30, 32-36, 39, 41, 42, 44-49, 51 and 52.

2. A diagnostic kit for MLPA analysis of the FcγRII/FcγRIII gene cluster, said kit comprising the assay probes of claim 1.

3. The diagnostic kit of claim 2 comprising at least one container having assay probes.

4. The diagnostic kit of claim 3 further comprising an additional container having assay probes comprising SEQ ID NOs: 25, 29, 31 and 38.

* * * * *

UNITED STATES PATENT AND TRADEMARK OFFICE
CERTIFICATE OF CORRECTION

| | | |
|---|---|---|
| PATENT NO. | : 7,994,300 B2 | Page 1 of 1 |
| APPLICATION NO. | : 12/158623 | |
| DATED | : August 9, 2011 | |
| INVENTOR(S) | : Roos et al. | |

It is certified that error appears in the above-identified patent and that said Letters Patent is hereby corrected as shown below:

ON THE COVER PAGE:

Now reads:

"(54)   DIAGNOSTIC METHODS INVOLVING DETERMINING GENE COPY NUMBERS AND SNPS IN THE FCYRII/FCYRIII GENE CLUSTER, AND PROBES FOR USE IN SUCH METHODS TO DETECT SUSCEPTIBILITY TO AND TREATMENT EFFICACY IN AUTOIMMUNE DISEASES"

Should read:

-- (54)   DIAGNOSTIC METHODS INVOLVING DETERMINING GENE COPY NUMBERS AND SNPs IN THE FcγRII/FcγRIII GENE CLUSTER, AND PROBES FOR USE IN SUCH METHODS TO DETECT SUSCEPTIBILITY TO AND TREATMENT EFFICACY IN AUTOIMMUNE DISEASES --

Signed and Sealed this
Twelfth Day of February, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 7,994,300 B2  
APPLICATION NO. : 12/158623  
DATED : August 9, 2011  
INVENTOR(S) : Roos et al.

Page 1 of 1

It is certified that error appears in the above-identified patent and that said Letters Patent is hereby corrected as shown below:

ON THE COVER PAGE, ITEM (54) AND AT COLUMN 1, LINES 1-7, TITLE

Now reads:

"DIAGNOSTIC METHODS INVOLVING DETERMINING GENE COPY NUMBERS AND SNPS IN THE FCYRII/FCYRIII GENE CLUSTER, AND PROBES FOR USE IN SUCH METHODS TO DETECT SUSCEPTIBILITY TO AND TREATMENT EFFICACY IN AUTOIMMUNE DISEASES"

Should read:

-- DIAGNOSTIC METHODS INVOLVING DETERMINING GENE COPY NUMBERS AND SNPs IN THE FcγRII/FcγRIII GENE CLUSTER, AND PROBES FOR USE IN SUCH METHODS TO DETECT SUSCEPTIBILITY TO AND TREATMENT EFFICACY IN AUTOIMMUNE DISEASES --

This certificate supersedes the Certificate of Correction issued February 12, 2013.

Signed and Sealed this  
Nineteenth Day of March, 2013

Teresa Stanek Rea  
*Acting Director of the United States Patent and Trademark Office*